US009428555B2

(12) United States Patent
Gu et al.

(10) Patent No.: US 9,428,555 B2
(45) **Date of Patent: *Aug. 30, 2016**

(54) TRUNCATED L1 PROTEIN OF HUMAN PAPILLOMAVIRUS TYPE 16

(75) Inventors: Ying Gu, Fujian (CN); Shaowei Li, Fujian (CN); Minxi Wei, Fujian (CN); Yangling Xian, Fujian (CN); Wenxin Luo, Fujian (CN); Ningshao Xia, Fujian (CN)

(73) Assignees: Beijing Wantai Biological Pharmacy Enterprise Co., Ltd., Beijing (CN); Xiamen University, Xiamen (CN)

( * ) Notice: Subject to any disclaimer, the term of this patent is extended or adjusted under 35 U.S.C. 154(b) by 698 days.

This patent is subject to a terminal disclaimer.

(21) Appl. No.: 12/598,186

(22) PCT Filed: Apr. 29, 2008

(86) PCT No.: PCT/CN2008/000872
§ 371 (c)(1), (2), (4) Date: Jun. 7, 2010

(87) PCT Pub. No.: WO2008/134934
PCT Pub. Date: Nov. 13, 2008

(65) Prior Publication Data

US 2010/0255031 A1 Oct. 7, 2010

(30) Foreign Application Priority Data

Apr. 29, 2007 (CN) .......................... 2007 1 0097762
Jan. 23, 2008 (CN) .......................... 2008 1 0008761

(51) Int. Cl.

| | |
|---|---|
| ***C07K 14/005*** | (2006.01) |
| ***A61K 39/12*** | (2006.01) |
| ***C12N 7/00*** | (2006.01) |
| *A61K 39/00* | (2006.01) |

(52) U.S. Cl.
CPC ............. *C07K 14/005* (2013.01); *A61K 39/12* (2013.01); *C12N 7/00* (2013.01); *A61K 2039/5258* (2013.01); *A61K 2039/55505* (2013.01); *A61K 2039/55566* (2013.01); *A61K 2039/70* (2013.01); *C12N 2710/20022* (2013.01); *C12N 2710/20034* (2013.01)

(58) Field of Classification Search
CPC ..................... A61K 39/12; A61K 2039/5258; C12N 2710/20023; C12N 2730/10123; C12N 2760/18534; C12N 2710/20034; C12N 2760/16123; C12N 2760/16234; C12N 2760/18634; C12N 2770/16034; C12N 2770/24134
See application file for complete search history.

(56) References Cited

U.S. PATENT DOCUMENTS

| | | | | |
|---|---|---|---|---|
| 5,820,870 | A | 10/1998 | Joyce et al. | |
| 5,840,306 | A * | 11/1998 | Hofmann et al. | 424/192.1 |
| 5,866,553 | A | 2/1999 | Donnelly et al. | |
| 6,013,262 | A | 1/2000 | Frazer et al. | |
| 6,066,324 | A | 5/2000 | Gissmann et al. | |
| 6,551,597 | B1 * | 4/2003 | Harrison et al. | 424/204.1 |
| 6,599,508 | B1 | 7/2003 | Gissmann et al. | |
| 6,602,697 | B1 | 8/2003 | Cook, III | |
| 6,649,167 | B2 | 11/2003 | Hallek et al. | |
| 6,908,615 | B1 * | 6/2005 | Hofmann et al. | 424/204.1 |
| 7,351,533 | B2 | 4/2008 | McCarthy et al. | |
| 7,709,010 | B2 | 5/2010 | Bryan et al. | |
| 7,754,430 | B2 | 7/2010 | Gissmann et al. | |
| 2002/0193565 | A1 * | 12/2002 | Stanley et al. | 530/350 |
| 2003/0118609 | A1 | 6/2003 | Harrison et al. | |
| 2004/0081661 | A1 | 4/2004 | Hallek et al. | |
| 2004/0202679 | A1 | 10/2004 | Gissmann et al. | |
| 2005/0031636 | A1 | 2/2005 | Gissmann et al. | |
| 2005/0175632 | A1 | 8/2005 | Wettendorff | |
| 2006/0153864 | A1 | 7/2006 | Gissmann et al. | |
| 2006/0198853 | A1 | 9/2006 | Gissmann et al. | |
| 2007/0036824 | A1 | 2/2007 | Bryan et al. | |
| 2007/0224218 | A1 | 9/2007 | Wettendorff | |
| 2008/0248062 | A1 | 10/2008 | Bryan et al. | |
| 2008/0279890 | A1 | 11/2008 | Wettendorff | |
| 2009/0028894 | A1 | 1/2009 | Gissmann et al. | |
| 2010/0255031 | A1 | 10/2010 | Gu et al. | |
| 2010/0272751 | A1 | 10/2010 | Li et al. | |
| 2010/0291141 | A1 | 11/2010 | Zhang et al. | |

FOREIGN PATENT DOCUMENTS

| | | |
|---|---|---|
| CN | 1185176 | 6/1998 |
| CN | 1478790 | 3/2004 |
| CN | 1578787 | 2/2005 |
| CN | 1642571 | 7/2005 |
| CN | 1683010 | 10/2005 |
| CN | 1821410 | 8/2006 |
| CN | 200710097762.8 | 4/2007 |
| CN | 200710097763.2 | 4/2007 |
| CN | 200810008731.5 | 1/2008 |
| CN | 200810008761.6 | 1/2008 |
| CN | 101153280 | 4/2008 |

(Continued)

OTHER PUBLICATIONS

Ma et al. Protein Expression and Purification 2007, vol. 56, pp. 72-79.*

Chen et al., "Papillomavirus Capsid Protein Expression in *Escherichia coli*: Purification and Assembly of HPV11 and HPV16 L1," *Journal of Molecular Biology*, vol. 307, No. 1, pp. 173-182, Mar. 16, 2001.

Chen et al., "Structure of Small Virus-Like Particles Assembled from the L1 protein of Human Papillomavirus 16," *Molecular Cell*, vol. 5, pp. 557-567, 2000.

(Continued)

*Primary Examiner* — Bao Li

(74) *Attorney, Agent, or Firm* — Fish & Richardson P.C.

(57) ABSTRACT

The invention relates to a truncated L1 protein of the Human Papillomavirus Type 16, a virus-like particle consisting of the protein, a vaccine comprising said virus-like particle, and the use of the vaccine in the prevention of cervical cancer.

17 Claims, 6 Drawing Sheets

(56) References Cited

FOREIGN PATENT DOCUMENTS

| | | |
|---|---|---|
| EP | 2 147 926 | 1/2010 |
| WO | 94/20137 | 9/1994 |
| WO | WO 96/29413 | 9/1996 |
| WO | WO 00/54730 | 9/2000 |
| WO | WO 02/43757 | 6/2002 |
| WO | WO 03/018624 | 3/2003 |
| WO | WO 03/077942 | 9/2003 |
| WO | WO 03/078455 | 9/2003 |
| WO | 03/093437 | 11/2003 |
| WO | 2004/056389 | 7/2004 |
| WO | 2008/134934 | 11/2008 |
| WO | WO 2008/134935 | 11/2008 |

OTHER PUBLICATIONS

European Search Report; Application No. 08748431.7-1223 / 2154147; mailed Oct. 4, 2011; (9 pages).

Bishop B, et. al. Virol J. Jan. 8, 2007;4:3.

Chen XS, Casini G, Harrison SC, Garcea RL. Papillomavirus capsid protein expression in *Escherichia coli*: purification and assembly of HPV11 and HPV16 L 1. J Mol BioI. Mar. 16, 2001;307(1):173-82.

Cho HJ, Oh YK, Kim VB. Advances in human papilloma virus vaccines: a patent review. Expert Opin Ther Pat. Mar. 2011;21 (3):295-309. Epub Jan. 21, 2011.

Dartmann K, Schwarz E, Gissmann L, zur Hausen H. The nucleotide sequence and genome organization of human papilloma virus type 11. Virology May 1986;151(1):124-30.

Final Office Action issued in U.S. Appl. No. 12/601,972 on Aug. 21, 2012 (8 pages).

Kelsall et al., "Expression of the Major Capsid Protein of Human Papillomavirus Type 16 in *Escherichia coli*," Journal of Virological Methods, Elsevier, BV, NL, 53(1) (1995).

Neeper et. al. HPV6 protein coding sequence. NCBI-GenBank. Acc. # AAC53712; submitted Apr. 19, 1996.

Office Action issued in U.S. Appl. No. 12/598,187 on Dec. 3, 2012 (6 pages).

Office Action issued in U.S. Appl. No. 12/598,187 on Jul. 12, 2013 (10 pages).

Office Action issued in U.S. Appl. No. 12/601,972 on Feb. 15, 2012 (8 pages).

Office Action issued in U.S. Appl. No. 12/601,972 on May 23, 2013 (23 pages).

RCE and Response to Final Office Action issued in U.S. Appl. No. 12/601,972 on Aug. 21, 2012 filed on Feb. 20, 2013 (17 pages).

Response to Office Action issued in U.S. Appl. No. 12/598,187 on Dec. 3, 2012 filed on May 3, 2013 (11 pages.

Response to Office Action issued in U.S. Appl. No. 12/601,972 on Feb. 15, 2012 filed on Jun. 14, 2012 (10 pages).

Response to Office Action issued in U.S. Appl. No. 12/601,972 on May 23, 2013 filed on Nov. 25, 2013 (21 pages).

Response to Restriction Requirement issued in U.S. Appl. No. 12/598,187 on Sep. 25, 2012 filed on Oct. 25, 2012 (2 pages).

Response to Restriction Requirement issued in U.S. Appl. No. 12/601,972 on Nov. 4, 2011 filed on Feb. 1, 2012 (8 pages).

Restriction Requirement issued in U.S. Appl. No. 12/598,187 on Sep. 25, 2012 (8 pages).

Restriction Requirement issued in U.S. Appl. No. 12/601,972 on Nov. 4, 2011 (7 pages).

Schiller JT, Castellsague X, Garland SM. A review of clinical trials of human papillomavirus prophylactic vaccines. Vaccine. Nov. 20, 2012;30 Suppl 5:F123-38.

Supplemental Response to Final Office Action issued in U.S. Appl. No. 12/601,972 on Aug. 21, 2012 filed on Apr. 1, 2013 (20 pages).

Caparros-Wanderley et al., "Intratype Sequence Variation Among Clinical Isolates of the Human Papillomavirus Type 6 L 1 ORF: Clustering of Mutations and Identification of a Frequent Amino Acid Sequence Variant"; Journal of General Virology, Apr. 1999; vol. 80, pp. 1025-1033.

Wang, Jiabi et al., "Expression of Recombinant HPV6 L 1 Protein in Prokaryotic System," Journal Clinical Dermatol, Jun. 2003, vol. 32, No. 6, ISSN 1000-4963.

Brief Communication issued in EP 08748431.7 on Dec. 9, 2013 (1 page).

Fang et al., "Post translational modifications of recombinant human Papillomavirus type 6b major capsid protein," Virus Research, 60(2):113-121 (1999).

Jana et al., "Strategies for efficient production of heterologous proteins in *Escherichia coli*," Applied Microbiology and Biotechnology, 67(3):289-298 (2005).

Luo et al., "Construction and application of an *Escherichia coli* high effective expression vector with an enhancer," Chinese Journal of Biotechnology, 16(5):578-581 (2000) (with English translation of Abstract).

Office Action issued in EP 08748431.7 on Dec. 5, 2013 (12 pages).

Bonnez et al., "Evolution of the antibody response to human papillomavirus type 11 (HPV-11) patients with condyloma acuminatum according to treatment response," J Med Virol., 1993, 39(4):340-344.

European Search Report corresponding to EP Application No. 08757380.4 dated Mar. 12, 2010.

European Office Action for Appln. No. 08 757 380.4 dated May 15, 2013, 7 pages.

European Search Report in Application No. 08757381.2 dated Jan. 27, 2014, 4 pages.

European Search Report in Application No. 08757381.2 dated Mar. 9, 2011, 5 pages.

Final office action issued in U.S. Appl. No. 12/601,972 on Feb. 27, 2014 (19 pages).

Li et al., "Expression of human papillomavirus type 11 L1 capsid protein in *Escherichia coli*: characterization of protein domains involved in DNA binding and capsid assembly," J Virol., Apr. 1997, 71(4):2988-95.

Office Action issued in U.S. Appl. No. 12/598,187 on Feb. 20, 2014 (6 pages).

Office Action issued in U.S. Appl. No. 12/601,983, dated Oct. 1, 2012, 8 pages.

Office Action issued in U.S. Appl. No. 12/601,983, dated Mar. 14, 2013, 11 pages.

Response to Office Action issued in U.S. Appl. No. 12/601,983 on Oct. 1, 2012 filed on Feb. 6, 2013 (10 pages).

Response to Restriction Requirement issued in U.S. Appl. No. 12/601,983 on Jul. 6, 2012 filed on Aug. 6, 2012 (7 pages).

Restriction Requirement issued in U.S. Appl. No. 12/601,983 on Jul. 6, 2012 (8 pages).

Rose et al., "Expression of human papillomavirus type 11 L1 protein in insect cells in-vivo and in-vitro assembly of viruslike particles," J Virol., Apr. 1993, 67(4):1936-1944.

Terminal Disclaimer in U.S. Appl. No. 12/601,983, filed Feb. 21, 2014, 1 page.

Villa et al., "Immunologic responses following administration of a vaccine targeting human papillomavirus Types 6, 11, 16 and 18," Vaccine, Jul. 7, 2006, 24(27-28):5571-83.

Written Opinion of International Searching Authority for PCT/CN2008/001050, English version, dated Sep. 11, 2008.

Xu et al., "Transformation activity 1-6 and the immunogenicity of a human papillomavirus type 16 variant E6E7 gene from cervical carcinoma biopsy in Shandong province," Xhonghua Weishengwuxue He Mianyixue Zazhi, Jul. 4, 2002, 22(4):427-432 (English Abstract).

Yan et al., "Expression, purification and immunogenicity of human papillomavirus type 11 virus-like particles from *Excherichia coli*," Weshengwu Xuebao, Nov. 2009, 49(11):1527-1533 (English Abstract).

Zhuang et al., "Construction and Identification of Prokaryotic Expression System with Ll Gene of Human Papillomavirus Type 11," Chinese J Endemiol., Mar. 20, 2004, 23(2):163-165 (English Abstract).

Appeal Brief filed in U.S. Appl. No. 12/601,983, filed Apr. 16, 2014, 17 pages.

Dwyer et al., "Computational Design of a Biologically Active Enzyme," Science, 304(5679):1967-1971 (Jun. 2004).

(56) References Cited

OTHER PUBLICATIONS

European Office Action issued in EP08757380.4-1405 dated Oct. 20, 2014.
Fey et al., "Demonstration of In Vitro Synthesis of Human Papilloma Viral Proteins from Hand and Foot Warts," J. Invest. Dermatol., 92:817-824 (1989).
Final Office Action issued in U.S. Appl. No. 12/601,983 on Feb. 13, 2015 (10 pages).
Murby et al., "Hydrophobicity Engineering to Increase Solubility and Stability of a Recombinant Protein from Respiratory Syncytial Virus," European Journal of Biochemistry, 230(1):38-44 (May 1995).
Nygren et al., "Engineering proteins to facilitate bioprocessing," Trends in Biotechnology, Elsevier Publications, Cambridge, GB, 12(5):184-188 (May 1994).
Office Action issued in EP08748432.5 on Feb. 5, 2015 (10 pages).
Office Action issued in U.S. Appl. No. 12/598,187, dated Feb. 23, 2015, 6 pages.
Schein et al., "Deletions at the C-terminus of Interferon Gamma Reduce RNA Binding and Activation of Double-Stranded-RNA cleavage by Bovine Seminal Ribonuclease," Biochemical Journal, 307(1):123-127 (1995).
Sterner, R., "BIOCHEMISTRY: De Novo Design of an Enzyme," Science, 304(5679):1916-1917 (Jun. 2004).
Cole et al., "Nucleotide sequence and comparative analysis of the human papillomavirus type 18 genome—Phylogeny of papillomaviruses and repeated structure of the E6 and E7 gene products," Journal of Molecular Biology 193:599-608, 1987.
European Search Report; Application No. 08748432.5-2406; mailed Dec. 23, 2011 (9 pages).
International Search Report; Application No. PCT/CN2008/000873; mailed Aug. 14, 2008; 7 pages.
International Search Report (in Chinese); Application No. PCT/CN2008/000872; pp. 1-9, Sep. 22, 2011.
Response to Office Action issued in U.S. Appl. No. 12/598,187, dated Sep. 30, 2014, filed on Jan. 29, 2015, 7 pages.
EMBL Database, Accession No. Q80B70, Jun. 1, 2003; 1 page.
European Office Action; Application No. 08748432.5-2406; mailed Nov. 27, 2012; Applicant: Beijing Wantai Biological Pharmacy Enterprise Co., Ltd. 6 pages.
European Communication; Application No. 0874831.7-1405; mailed Feb. 14, 2013; 7 pages.
Office Action issued in U.S. Appl. No. 12/598,187, dated Dec. 3, 2012, 6 pages.
Response to Office Action issued in U.S. Appl. No. 12/598,187, dated Dec. 3, 2012 filed on May 3, 2013, 11 pages.
Office Action issued in U.S. Appl. No. 12/598,187, dated Jul. 12, 2013, 10 pages.
Response to Office Action issued in U.S. Appl. No. 12/598,187, dated Jul. 12, 2013 filed on Jan. 8, 2014, 8 pages.
Response to Office Action issued in U.S. Appl. No. 12/598,187 on Feb. 20, 2014 filed on Aug. 20, 2014, 7 pages.
Office Action issued in U.S. Appl. No. 12/598,187, dated Sep. 30, 2014, 6 pages.
Office Action issued in U.S. Appl. No. 12/601,983 dated Aug. 28, 2014, 14 pages.
Gen Bank: AAA46935.1. major capsid protein [Human papillomavirus type 11], Jun. 4, 1994. http://www.ncbi.nlm.nih.gov/protein/496201.
Gen Bank: AAQ92369.1, HPV18 major capsid protein L 1 [synthetic construct], Oct. 11, 2003 http://www.ncbi.nlm.nih.gov/protein/375288783?report=genbank&log$=protalign&blast_rank=1&RID=V8ACF90G015.
GenBank: AAC80442.1, major capsid protein [Human papillomavirus type 6], Apr. 13, 1999 http://www.ncbi.nlm.nih.gov/protein/3930543?report=genbank&log$=protalign&blast_rank=1&RID=V88RAMAW014.
Gen Bank: AAC09292.1, late major capsid protein [Human papillomavirus type 16], Apr. 2, 1998 http://www.ncbi.nlm.nih.gov/protein/3005059?report=genbank&log$=protalign&blast_rank=4&RI.
Response to Office Action issued in U.S. Appl. No. 12/601,983 on Aug. 28, 2014 filed on Dec. 23, 2014 (6 pages).
Request Under AFCP and Response to Final Office Action issued in U.S. Appl. No. 12/601,983 on Feb. 13, 2015 filed on Apr. 13, 2015 (8 pages).
Response to Restriction Requirement issued in U.S. Appl. No. 14/248,063 on Jan. 21, 2015 filed on Mar. 23, 2015 (2 pages).
Restriction Requirement issued in U.S. Appl. No. 14/248,063 on Jan. 21, 2015 (6 pages).
Response to Office Action issued in U.S. Appl. No. 12/598,187, dated Feb. 23, 2015 filed on May 6, 2015 (7 pages).
Office Action issued in U.S. Appl. No. 12/601,983 on May 13, 2015 (10 pages).
Office Action issued in U.S. Appl. No. 14/248,063 on Jun. 10, 2015 (21 pages).
Casini et al., "In vitro papillomavirus capsid assembly analyzed by light scattering," Virology, 325(2):320-327 (Aug. 1, 2004).
Chen et al., "Structure of small virus-like particles assembled from the L1 protein of human papillomavirus 16," Molecular Cell, 5(3):557-567 (Mar. 1, 2000).
European Search Report dated Jul. 22, 2015 for Appln. No. 15160339.0 (8 pages).
European Search Report dated Jul. 27, 2015 for Appln. No. 15160363.6 (11 pages).
Indian Office Action dated Jul. 27, 2015 for Appln. No. 8058/DELNP/2009.
Kelsall et al., "Expression of the major capsid protein of human papillomavirus type 16 in *Escherichia coli*," Journal of Virological Methods, 53(1):75-90 (Jan. 1, 1995).
Li et al., "Expression of the human papillomavirus type 11 L1 capsid protein in *Escherichia coli*: characterization of protein domains involved in DNA binding and capsid assembly," Journal of Virlogy, The American Society for Microbiology, 71:2988-2995 (Apr. 1, 1997).
Neeper et al., "Expression of the major capsid protein of human papillomavirus type 11 in *Saccharomyces cerevisae*," Gene, 180(1-2):1-6 (Nov. 21, 1996).
Office Action issued in U.S. Appl. No. 12/601,983 on Sep. 8, 2015 (10 pages).
Response to Office Action issued in U.S. Appl. No. 14/248,063 on Jun. 10, 2015 filed on Sep. 29, 2015 (15 pages).
Xu et al., "Papillomavirus virus-like particles as vehicles for the delivery of epitopes or genes," Archives of Virology, 151(11):2133-2148 (Jun. 22, 2006).
Zhang et al., "Expression of human papillomavirus type 16 L1 protein in *escherichia coli*: denaturation, renaturation, and self-assembly of virus-like particles in vitro," Virology, 243(2):423-431 (Apr. 10, 1998).
Cheng et al., "Construction of Recombinant Plasmid pQE32-HPV18 L1 and Protein Expression," Chinese Journal of Nosocomiology 15:845-848, 2005.
EMBL Database, Accession No. Q80B70, Jun. 1, 2003, 1 page.
European Office Action; Application No. 08748432.5-2406; mailed Nov. 27, 2012; Applicant: Beijing Wantai Biological Pharmacy Enterprise Co., Ltd., 6 pages.
European Communications; Application No. 08748431.7-1405; mailed Feb. 14, 2013; 7 pages.
Janine T. Bryan, "Developing an HPV Vaccine to Prevent Cervical Cancer and Genital Warts," *Vaccine* 28:3001-3006; 2007.
Response to Office Action issued in U.S. Appl. No. 12/601,983 on Sep. 8, 2015, filed on Dec. 4, 2015 (6 pages).
Office Action issued in U.S. Appl. No. 12/598,187 on Nov. 19, 2015 (5 pages).
Response to Office Action issued in U.S. Appl. No. 12/598,187 on Nov. 19, 2015, filed on Jan. 7, 2016 (10 pages).

(56) References Cited

OTHER PUBLICATIONS

Final Office Action issued in U.S. Appl. No. 14/248,063 on Jan. 6, 2016 (18 pages).
European Molecular Biology Laboratory (EMBL), "Extraction and Clarification: Preparation of cell lysates from *E. Coli*, " http://www.embl.de/pepcore/pepcore__serives/protein__purification/extraction__clarification/cell__lysates__ecoli/enzymatic__lysis/, accessed Dec. 30, 2015, Available online Feb. 1, 2002.
McCarthy et al., "Quantitative disassembly and reasembly of human papillomavirus type 11 viruslike particles in vitro," J. Virol., 72(1):32-41 (1998).
Final Office Action issued in U.S. Appl. No. 12/601,983 on Dec. 22, 2015 (10 pages).

* cited by examiner

SEQUENCE LISTING

```
<160> NUMBER OF SEQ ID NOS: 15

<210> SEQ ID NO 1
<211> LENGTH: 528
<212> TYPE: PRT
<213> ORGANISM: Artificial sequence
<220> FEATURE:
<223> OTHER INFORMATION: Synthesized in the laboratory

<400> SEQUENCE: 1

Met Phe Ile Tyr Ile Leu Val Ile Thr Cys Tyr Glu Asn Asp Val Asn
1               5                   10                  15

Val Tyr His Ile Phe Phe Gln Met Ser Leu Trp Leu Pro Ser Glu Ala
            20                  25                  30

Thr Val Tyr Leu Pro Pro Val Pro Val Ser Lys Val Val Ser Thr Asp
        35                  40                  45

Glu Tyr Val Ala Arg Thr Asn Ile Tyr Tyr His Ala Gly Thr Ser Arg
    50                  55                  60

Leu Leu Ala Val Gly His Pro Tyr Phe Pro Ile Lys Lys Pro Asn Asn
65                  70                  75                  80

Asn Lys Ile Leu Val Pro Lys Val Ser Gly Leu Gln Tyr Arg Val Phe
                85                  90                  95

Arg Ile His Leu Pro Asp Pro Asn Lys Phe Gly Phe Pro Asp Thr Ser
            100                 105                 110

Phe Tyr Asn Pro Asp Thr Gln Arg Leu Val Trp Ala Cys Val Gly Val
        115                 120                 125

Glu Val Gly Arg Gly Gln Pro Leu Gly Val Gly Ile Ser Gly His Pro
    130                 135                 140
```

```
Leu Leu Asn Lys Leu Asp Asp Thr Glu Asn Ala Ser Ala Tyr Ala Ala
145                 150                 155                 160

Asn Ala Gly Val Asp Asn Arg Glu Cys Ile Ser Met Asp Tyr Lys Gln
                165                 170                 175

Thr Gln Leu Cys Leu Ile Gly Cys Lys Pro Pro Ile Gly Glu His Trp
            180                 185                 190

Gly Lys Gly Ser Pro Cys Thr Asn Val Ala Val Asn Pro Gly Asp Cys
        195                 200                 205

Pro Pro Leu Glu Leu Ile Asn Thr Val Ile Gln Asp Gly Asp Met Val
    210                 215                 220

Asp Thr Gly Phe Gly Ala Met Asp Phe Thr Thr Leu Gln Ala Asn Lys
225                 230                 235                 240

Ser Glu Val Pro Leu Asp Ile Cys Thr Ser Ile Cys Lys Tyr Pro Asp
                245                 250                 255

Tyr Ile Lys Met Val Ser Glu Pro Tyr Gly Asp Ser Leu Phe Phe Tyr
            260                 265                 270

Leu Arg Arg Glu Gln Met Phe Val Arg His Leu Phe Asn Arg Ala Gly
        275                 280                 285

Ala Val Gly Asp Asn Val Pro Asp Asp Leu Tyr Ile Lys Gly Ser Gly
    290                 295                 300

Ser Thr Ala Asn Leu Ala Ser Ser Asn Tyr Phe Pro Thr Pro Ser Gly
305                 310                 315                 320

Ser Met Val Thr Ser Asp Ala Gln Ile Phe Asn Lys Pro Tyr Trp Leu
                325                 330                 335

Gln Arg Ala Gln Gly His Asn Asn Gly Ile Cys Trp Gly Asn Gln Leu
            340                 345                 350

Phe Val Thr Val Val Asp Thr Thr Arg Ser Thr Asn Met Ser Leu Cys
        355                 360                 365

Ala Ala Ile Ser Thr Ser Glu Thr Thr Tyr Lys Asn Thr Asn Phe Lys
    370                 375                 380

Glu Tyr Leu Arg His Gly Glu Glu Tyr Asp Leu Gln Phe Ile Phe Gln
385                 390                 395                 400

Leu Cys Lys Ile Thr Leu Thr Ala Asp Ile Met Thr Tyr Ile His Ser
                405                 410                 415

Met Asn Ser Thr Ile Leu Glu Asp Trp Asn Phe Gly Leu Gln Pro Pro
            420                 425                 430

Pro Gly Gly Thr Leu Glu Asp Thr Tyr Arg Phe Val Thr Ser Gln Ala
        435                 440                 445

Ile Ala Cys Gln Lys His Thr Pro Pro Ala Pro Lys Glu Asp Pro Leu
    450                 455                 460

Lys Lys Tyr Thr Phe Trp Glu Val Asn Leu Lys Glu Lys Phe Ser Ala
465                 470                 475                 480

Asp Leu Asp Gln Phe Pro Leu Gly Arg Lys Phe Leu Leu Gln Ala Gly
                485                 490                 495

Leu Glu Ala Lys Pro Lys Phe Thr Leu Gly Lys Arg Lys Ala Thr Pro
            500                 505                 510

Thr Thr Ser Ser Thr Ser Thr Thr Ala Lys Arg Lys Lys Arg Lys Leu
        515                 520                 525
```

<210> SEQ ID NO 2
<211> LENGTH: 526
<212> TYPE: PRT
<213> ORGANISM: Artificial sequence
<220> FEATURE:
<223> OTHER INFORMATION: Synthesized in the laboratory

<400> SEQUENCE: 2

```
Met Tyr Ile Leu Val Ile Thr Cys Tyr Glu Asn Asp Val Asn Val Tyr
1               5                   10                  15

His Ile Phe Phe Gln Met Ser Leu Trp Leu Pro Ser Glu Ala Thr Val
            20                  25                  30

Tyr Leu Pro Pro Val Pro Val Ser Lys Val Val Ser Thr Asp Glu Tyr
        35                  40                  45

Val Ala Arg Thr Asn Ile Tyr Tyr His Ala Gly Thr Ser Arg Leu Leu
    50                  55                  60

Ala Val Gly His Pro Tyr Phe Pro Ile Lys Lys Pro Asn Asn Asn Lys
65                  70                  75                  80

Ile Leu Val Pro Lys Val Ser Gly Leu Gln Tyr Arg Val Phe Arg Ile
                85                  90                  95

His Leu Pro Asp Pro Asn Lys Phe Gly Phe Pro Asp Thr Ser Phe Tyr
            100                 105                 110

Asn Pro Asp Thr Gln Arg Leu Val Trp Ala Cys Val Gly Val Glu Val
        115                 120                 125

Gly Arg Gly Gln Pro Leu Gly Val Gly Ile Ser Gly His Pro Leu Leu
    130                 135                 140

Asn Lys Leu Asp Asp Thr Glu Asn Ala Ser Ala Tyr Ala Ala Asn Ala
145                 150                 155                 160

Gly Val Asp Asn Arg Glu Cys Ile Ser Met Asp Tyr Lys Gln Thr Gln
                165                 170                 175

Leu Cys Leu Ile Gly Cys Lys Pro Pro Ile Gly Glu His Trp Gly Lys
            180                 185                 190

Gly Ser Pro Cys Thr Asn Val Ala Val Asn Pro Gly Asp Cys Pro Pro
        195                 200                 205

Leu Glu Leu Ile Asn Thr Val Ile Gln Asp Gly Asp Met Val Asp Thr
    210                 215                 220

Gly Phe Gly Ala Met Asp Phe Thr Thr Leu Gln Ala Asn Lys Ser Glu
225                 230                 235                 240

Val Pro Leu Asp Ile Cys Thr Ser Ile Cys Lys Tyr Pro Asp Tyr Ile
                245                 250                 255

Lys Met Val Ser Glu Pro Tyr Gly Asp Ser Leu Phe Phe Tyr Leu Arg
            260                 265                 270

Arg Glu Gln Met Phe Val Arg His Leu Phe Asn Arg Ala Gly Ala Val
        275                 280                 285

Gly Asp Asn Val Pro Asp Asp Leu Tyr Ile Lys Gly Ser Gly Ser Thr
    290                 295                 300

Ala Asn Leu Ala Ser Ser Asn Tyr Phe Pro Thr Pro Ser Gly Ser Met
305                 310                 315                 320

Val Thr Ser Asp Ala Gln Ile Phe Asn Lys Pro Tyr Trp Leu Gln Arg
                325                 330                 335

Ala Gln Gly His Asn Asn Gly Ile Cys Trp Gly Asn Gln Leu Phe Val
            340                 345                 350

Thr Val Val Asp Thr Thr Arg Ser Thr Asn Met Ser Leu Cys Ala Ala
        355                 360                 365

Ile Ser Thr Ser Glu Thr Thr Tyr Lys Asn Thr Asn Phe Lys Glu Tyr
    370                 375                 380

Leu Arg His Gly Glu Glu Tyr Asp Leu Gln Phe Ile Phe Gln Leu Cys
385                 390                 395                 400

Lys Ile Thr Leu Thr Ala Asp Ile Met Thr Tyr Ile His Ser Met Asn
```

```
                405                 410                 415

Ser Thr Ile Leu Glu Asp Trp Asn Phe Gly Leu Gln Pro Pro Pro Gly
            420                 425                 430

Gly Thr Leu Glu Asp Thr Tyr Arg Phe Val Thr Ser Gln Ala Ile Ala
        435                 440                 445

Cys Gln Lys His Thr Pro Pro Ala Pro Lys Glu Asp Pro Leu Lys Lys
    450                 455                 460

Tyr Thr Phe Trp Glu Val Asn Leu Lys Glu Lys Phe Ser Ala Asp Leu
465                 470                 475                 480

Asp Gln Phe Pro Leu Gly Arg Lys Phe Leu Leu Gln Ala Gly Leu Glu
                485                 490                 495

Ala Lys Pro Lys Phe Thr Leu Gly Lys Arg Lys Ala Thr Pro Thr Thr
            500                 505                 510

Ser Ser Thr Ser Thr Thr Ala Lys Arg Lys Lys Arg Lys Leu
        515                 520                 525


<210> SEQ ID NO 3
<211> LENGTH: 524
<212> TYPE: PRT
<213> ORGANISM: Artificial sequence
<220> FEATURE:
<223> OTHER INFORMATION: Synthesized in the laboratory

<400> SEQUENCE: 3

Met Leu Val Ile Thr Cys Tyr Glu Asn Asp Val Asn Val Tyr His Ile
1               5                   10                  15

Phe Phe Gln Met Ser Leu Trp Leu Pro Ser Glu Ala Thr Val Tyr Leu
            20                  25                  30

Pro Pro Val Pro Val Ser Lys Val Val Ser Thr Asp Glu Tyr Val Ala
        35                  40                  45

Arg Thr Asn Ile Tyr Tyr His Ala Gly Thr Ser Arg Leu Leu Ala Val
    50                  55                  60

Gly His Pro Tyr Phe Pro Ile Lys Lys Pro Asn Asn Asn Lys Ile Leu
65                  70                  75                  80

Val Pro Lys Val Ser Gly Leu Gln Tyr Arg Val Phe Arg Ile His Leu
                85                  90                  95

Pro Asp Pro Asn Lys Phe Gly Phe Pro Asp Thr Ser Phe Tyr Asn Pro
            100                 105                 110

Asp Thr Gln Arg Leu Val Trp Ala Cys Val Gly Val Glu Val Gly Arg
        115                 120                 125

Gly Gln Pro Leu Gly Val Gly Ile Ser Gly His Pro Leu Leu Asn Lys
    130                 135                 140

Leu Asp Asp Thr Glu Asn Ala Ser Ala Tyr Ala Ala Asn Ala Gly Val
145                 150                 155                 160

Asp Asn Arg Glu Cys Ile Ser Met Asp Tyr Lys Gln Thr Gln Leu Cys
                165                 170                 175

Leu Ile Gly Cys Lys Pro Pro Ile Gly Glu His Trp Gly Lys Gly Ser
            180                 185                 190

Pro Cys Thr Asn Val Ala Val Asn Pro Gly Asp Cys Pro Pro Leu Glu
        195                 200                 205

Leu Ile Asn Thr Val Ile Gln Asp Gly Asp Met Val Asp Thr Gly Phe
    210                 215                 220

Gly Ala Met Asp Phe Thr Thr Leu Gln Ala Asn Lys Ser Glu Val Pro
225                 230                 235                 240

Leu Asp Ile Cys Thr Ser Ile Cys Lys Tyr Pro Asp Tyr Ile Lys Met
```

```
                245                 250                 255

Val Ser Glu Pro Tyr Gly Asp Ser Leu Phe Phe Tyr Leu Arg Arg Glu
            260                 265                 270

Gln Met Phe Val Arg His Leu Phe Asn Arg Ala Gly Ala Val Gly Asp
        275                 280                 285

Asn Val Pro Asp Asp Leu Tyr Ile Lys Gly Ser Gly Ser Thr Ala Asn
    290                 295                 300

Leu Ala Ser Ser Asn Tyr Phe Pro Thr Pro Ser Gly Ser Met Val Thr
305                 310                 315                 320

Ser Asp Ala Gln Ile Phe Asn Lys Pro Tyr Trp Leu Gln Arg Ala Gln
                325                 330                 335

Gly His Asn Asn Gly Ile Cys Trp Gly Asn Gln Leu Phe Val Thr Val
            340                 345                 350

Val Asp Thr Thr Arg Ser Thr Asn Met Ser Leu Cys Ala Ala Ile Ser
        355                 360                 365

Thr Ser Glu Thr Thr Tyr Lys Asn Thr Asn Phe Lys Glu Tyr Leu Arg
    370                 375                 380

His Gly Glu Glu Tyr Asp Leu Gln Phe Ile Phe Gln Leu Cys Lys Ile
385                 390                 395                 400

Thr Leu Thr Ala Asp Ile Met Thr Tyr Ile His Ser Met Asn Ser Thr
                405                 410                 415

Ile Leu Glu Asp Trp Asn Phe Gly Leu Gln Pro Pro Pro Gly Gly Thr
            420                 425                 430

Leu Glu Asp Thr Tyr Arg Phe Val Thr Ser Gln Ala Ile Ala Cys Gln
        435                 440                 445

Lys His Thr Pro Pro Ala Pro Lys Glu Asp Pro Leu Lys Lys Tyr Thr
    450                 455                 460

Phe Trp Glu Val Asn Leu Lys Glu Lys Phe Ser Ala Asp Leu Asp Gln
465                 470                 475                 480

Phe Pro Leu Gly Arg Lys Phe Leu Leu Gln Ala Gly Leu Glu Ala Lys
                485                 490                 495

Pro Lys Phe Thr Leu Gly Lys Arg Lys Ala Thr Pro Thr Thr Ser Ser
            500                 505                 510

Thr Ser Thr Thr Ala Lys Arg Lys Lys Arg Lys Leu
        515                 520


<210> SEQ ID NO 4
<211> LENGTH: 522
<212> TYPE: PRT
<213> ORGANISM: Artificial sequence
<220> FEATURE:
<223> OTHER INFORMATION: Synthesized in the laboratory

<400> SEQUENCE: 4

Met Ile Thr Cys Tyr Glu Asn Asp Val Asn Val Tyr His Ile Phe Phe
1               5                   10                  15

Gln Met Ser Leu Trp Leu Pro Ser Glu Ala Thr Val Tyr Leu Pro Pro
            20                  25                  30

Val Pro Val Ser Lys Val Val Ser Thr Asp Glu Tyr Val Ala Arg Thr
        35                  40                  45

Asn Ile Tyr Tyr His Ala Gly Thr Ser Arg Leu Leu Ala Val Gly His
    50                  55                  60

Pro Tyr Phe Pro Ile Lys Lys Pro Asn Asn Asn Lys Ile Leu Val Pro
65                  70                  75                  80

Lys Val Ser Gly Leu Gln Tyr Arg Val Phe Arg Ile His Leu Pro Asp
```

-continued

```
                85                  90                  95

Pro Asn Lys Phe Gly Phe Pro Asp Thr Ser Phe Tyr Asn Pro Asp Thr
            100                 105                 110

Gln Arg Leu Val Trp Ala Cys Val Gly Val Glu Val Gly Arg Gly Gln
        115                 120                 125

Pro Leu Gly Val Gly Ile Ser Gly His Pro Leu Leu Asn Lys Leu Asp
    130                 135                 140

Asp Thr Glu Asn Ala Ser Ala Tyr Ala Ala Asn Ala Gly Val Asp Asn
145                 150                 155                 160

Arg Glu Cys Ile Ser Met Asp Tyr Lys Gln Thr Gln Leu Cys Leu Ile
                165                 170                 175

Gly Cys Lys Pro Pro Ile Gly Glu His Trp Gly Lys Gly Ser Pro Cys
            180                 185                 190

Thr Asn Val Ala Val Asn Pro Gly Asp Cys Pro Pro Leu Glu Leu Ile
        195                 200                 205

Asn Thr Val Ile Gln Asp Gly Asp Met Val Asp Thr Gly Phe Gly Ala
    210                 215                 220

Met Asp Phe Thr Thr Leu Gln Ala Asn Lys Ser Glu Val Pro Leu Asp
225                 230                 235                 240

Ile Cys Thr Ser Ile Cys Lys Tyr Pro Asp Tyr Ile Lys Met Val Ser
                245                 250                 255

Glu Pro Tyr Gly Asp Ser Leu Phe Phe Tyr Leu Arg Arg Glu Gln Met
            260                 265                 270

Phe Val Arg His Leu Phe Asn Arg Ala Gly Ala Val Gly Asp Asn Val
        275                 280                 285

Pro Asp Asp Leu Tyr Ile Lys Gly Ser Gly Ser Thr Ala Asn Leu Ala
    290                 295                 300

Ser Ser Asn Tyr Phe Pro Thr Pro Ser Gly Ser Met Val Thr Ser Asp
305                 310                 315                 320

Ala Gln Ile Phe Asn Lys Pro Tyr Trp Leu Gln Arg Ala Gln Gly His
                325                 330                 335

Asn Asn Gly Ile Cys Trp Gly Asn Gln Leu Phe Val Thr Val Val Asp
            340                 345                 350

Thr Thr Arg Ser Thr Asn Met Ser Leu Cys Ala Ala Ile Ser Thr Ser
        355                 360                 365

Glu Thr Thr Tyr Lys Asn Thr Asn Phe Lys Glu Tyr Leu Arg His Gly
    370                 375                 380

Glu Glu Tyr Asp Leu Gln Phe Ile Phe Gln Leu Cys Lys Ile Thr Leu
385                 390                 395                 400

Thr Ala Asp Ile Met Thr Tyr Ile His Ser Met Asn Ser Thr Ile Leu
                405                 410                 415

Glu Asp Trp Asn Phe Gly Leu Gln Pro Pro Pro Gly Gly Thr Leu Glu
            420                 425                 430

Asp Thr Tyr Arg Phe Val Thr Ser Gln Ala Ile Ala Cys Gln Lys His
        435                 440                 445

Thr Pro Pro Ala Pro Lys Glu Asp Pro Leu Lys Lys Tyr Thr Phe Trp
    450                 455                 460

Glu Val Asn Leu Lys Glu Lys Phe Ser Ala Asp Leu Asp Gln Phe Pro
465                 470                 475                 480

Leu Gly Arg Lys Phe Leu Leu Gln Ala Gly Leu Glu Ala Lys Pro Lys
                485                 490                 495

Phe Thr Leu Gly Lys Arg Lys Ala Thr Pro Thr Thr Ser Ser Thr Ser
            500                 505                 510
```

```
Thr Thr Ala Lys Arg Lys Lys Arg Lys Leu
        515                 520


<210> SEQ ID NO 5
<211> LENGTH: 512
<212> TYPE: PRT
<213> ORGANISM: Artificial sequence
<220> FEATURE:
<223> OTHER INFORMATION: Synthesized in the laboratory

<400> SEQUENCE: 5

Met Tyr His Ile Phe Phe Gln Met Ser Leu Trp Leu Pro Ser Glu Ala
1               5                   10                  15

Thr Val Tyr Leu Pro Pro Val Pro Val Ser Lys Val Val Ser Thr Asp
            20                  25                  30

Glu Tyr Val Ala Arg Thr Asn Ile Tyr Tyr His Ala Gly Thr Ser Arg
        35                  40                  45

Leu Leu Ala Val Gly His Pro Tyr Phe Pro Ile Lys Lys Pro Asn Asn
    50                  55                  60

Asn Lys Ile Leu Val Pro Lys Val Ser Gly Leu Gln Tyr Arg Val Phe
65                  70                  75                  80

Arg Ile His Leu Pro Asp Pro Asn Lys Phe Gly Phe Pro Asp Thr Ser
                85                  90                  95

Phe Tyr Asn Pro Asp Thr Gln Arg Leu Val Trp Ala Cys Val Gly Val
            100                 105                 110

Glu Val Gly Arg Gly Gln Pro Leu Gly Val Gly Ile Ser Gly His Pro
        115                 120                 125

Leu Leu Asn Lys Leu Asp Asp Thr Glu Asn Ala Ser Ala Tyr Ala Ala
    130                 135                 140

Asn Ala Gly Val Asp Asn Arg Glu Cys Ile Ser Met Asp Tyr Lys Gln
145                 150                 155                 160

Thr Gln Leu Cys Leu Ile Gly Cys Lys Pro Pro Ile Gly Glu His Trp
                165                 170                 175

Gly Lys Gly Ser Pro Cys Thr Asn Val Ala Val Asn Pro Gly Asp Cys
            180                 185                 190

Pro Pro Leu Glu Leu Ile Asn Thr Val Ile Gln Asp Gly Asp Met Val
        195                 200                 205

Asp Thr Gly Phe Gly Ala Met Asp Phe Thr Thr Leu Gln Ala Asn Lys
    210                 215                 220

Ser Glu Val Pro Leu Asp Ile Cys Thr Ser Ile Cys Lys Tyr Pro Asp
225                 230                 235                 240

Tyr Ile Lys Met Val Ser Glu Pro Tyr Gly Asp Ser Leu Phe Phe Tyr
                245                 250                 255

Leu Arg Arg Glu Gln Met Phe Val Arg His Leu Phe Asn Arg Ala Gly
            260                 265                 270

Ala Val Gly Asp Asn Val Pro Asp Asp Leu Tyr Ile Lys Gly Ser Gly
        275                 280                 285

Ser Thr Ala Asn Leu Ala Ser Ser Asn Tyr Phe Pro Thr Pro Ser Gly
    290                 295                 300

Ser Met Val Thr Ser Asp Ala Gln Ile Phe Asn Lys Pro Tyr Trp Leu
305                 310                 315                 320

Gln Arg Ala Gln Gly His Asn Asn Gly Ile Cys Trp Gly Asn Gln Leu
                325                 330                 335

Phe Val Thr Val Val Asp Thr Thr Arg Ser Thr Asn Met Ser Leu Cys
            340                 345                 350
```

```
Ala Ala Ile Ser Thr Ser Glu Thr Thr Tyr Lys Asn Thr Asn Phe Lys
        355                 360                 365

Glu Tyr Leu Arg His Gly Glu Glu Tyr Asp Leu Gln Phe Ile Phe Gln
    370                 375                 380

Leu Cys Lys Ile Thr Leu Thr Ala Asp Ile Met Thr Tyr Ile His Ser
385                 390                 395                 400

Met Asn Ser Thr Ile Leu Glu Asp Trp Asn Phe Gly Leu Gln Pro Pro
                405                 410                 415

Pro Gly Gly Thr Leu Glu Asp Thr Tyr Arg Phe Val Thr Ser Gln Ala
            420                 425                 430

Ile Ala Cys Gln Lys His Thr Pro Pro Ala Pro Lys Glu Asp Pro Leu
        435                 440                 445

Lys Lys Tyr Thr Phe Trp Glu Val Asn Leu Lys Glu Lys Phe Ser Ala
    450                 455                 460

Asp Leu Asp Gln Phe Pro Leu Gly Arg Lys Phe Leu Leu Gln Ala Gly
465                 470                 475                 480

Leu Glu Ala Lys Pro Lys Phe Thr Leu Gly Lys Arg Lys Ala Thr Pro
                485                 490                 495

Thr Thr Ser Ser Thr Ser Thr Thr Ala Lys Arg Lys Lys Arg Lys Leu
            500                 505                 510


<210> SEQ ID NO 6
<211> LENGTH: 502
<212> TYPE: PRT
<213> ORGANISM: Artificial sequence
<220> FEATURE:
<223> OTHER INFORMATION: Synthesized in the laboratory

<400> SEQUENCE: 6

Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Phe Pro
        35                  40                  45

Ile Lys Lys Pro Asn Asn Asn Lys Ile Leu Val Pro Lys Val Ser Gly
    50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
    130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205
```

```
Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285

Phe Pro Thr Pro Ser Gly Ser Met Val Thr Ser Asp Ala Gln Ile Phe
    290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400

Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
    450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
            500


<210> SEQ ID NO 7
<211> LENGTH: 492
<212> TYPE: PRT
<213> ORGANISM: Artificial sequence
<220> FEATURE:
<223> OTHER INFORMATION: Synthesized in the laboratory

<400> SEQUENCE: 7

Met Pro Val Pro Val Ser Lys Val Val Ser Thr Asp Glu Tyr Val Ala
1               5                   10                  15

Arg Thr Asn Ile Tyr Tyr His Ala Gly Thr Ser Arg Leu Leu Ala Val
            20                  25                  30

Gly His Pro Tyr Phe Pro Ile Lys Lys Pro Asn Asn Asn Lys Ile Leu
        35                  40                  45

Val Pro Lys Val Ser Gly Leu Gln Tyr Arg Val Phe Arg Ile His Leu
    50                  55                  60
```

```
Pro Asp Pro Asn Lys Phe Gly Phe Pro Asp Thr Ser Phe Tyr Asn Pro
65                  70                  75                  80

Asp Thr Gln Arg Leu Val Trp Ala Cys Val Gly Val Glu Val Gly Arg
                85                  90                  95

Gly Gln Pro Leu Gly Val Gly Ile Ser Gly His Pro Leu Leu Asn Lys
            100                 105                 110

Leu Asp Asp Thr Glu Asn Ala Ser Ala Tyr Ala Ala Asn Ala Gly Val
        115                 120                 125

Asp Asn Arg Glu Cys Ile Ser Met Asp Tyr Lys Gln Thr Gln Leu Cys
    130                 135                 140

Leu Ile Gly Cys Lys Pro Pro Ile Gly Glu His Trp Gly Lys Gly Ser
145                 150                 155                 160

Pro Cys Thr Asn Val Ala Val Asn Pro Gly Asp Cys Pro Pro Leu Glu
                165                 170                 175

Leu Ile Asn Thr Val Ile Gln Asp Gly Asp Met Val Asp Thr Gly Phe
            180                 185                 190

Gly Ala Met Asp Phe Thr Thr Leu Gln Ala Asn Lys Ser Glu Val Pro
        195                 200                 205

Leu Asp Ile Cys Thr Ser Ile Cys Lys Tyr Pro Asp Tyr Ile Lys Met
    210                 215                 220

Val Ser Glu Pro Tyr Gly Asp Ser Leu Phe Phe Tyr Leu Arg Arg Glu
225                 230                 235                 240

Gln Met Phe Val Arg His Leu Phe Asn Arg Ala Gly Ala Val Gly Glu
                245                 250                 255

Asn Val Pro Asp Asp Leu Tyr Ile Lys Gly Ser Gly Ser Thr Ala Asn
            260                 265                 270

Leu Ala Ser Ser Asn Tyr Phe Pro Thr Pro Ser Gly Ser Met Val Thr
        275                 280                 285

Ser Asp Ala Gln Ile Phe Asn Lys Pro Tyr Trp Leu Gln Arg Ala Gln
    290                 295                 300

Gly His Asn Asn Gly Ile Cys Trp Gly Asn Gln Leu Phe Val Thr Val
305                 310                 315                 320

Val Asp Thr Thr Arg Ser Thr Asn Met Ser Leu Cys Ala Ala Ile Ser
                325                 330                 335

Thr Ser Glu Thr Thr Tyr Lys Asn Thr Asn Phe Lys Glu Tyr Leu Arg
            340                 345                 350

His Gly Glu Glu Tyr Asp Leu Gln Phe Ile Phe Gln Leu Cys Lys Ile
        355                 360                 365

Thr Leu Thr Ala Asp Val Met Thr Tyr Ile His Ser Met Asn Ser Thr
    370                 375                 380

Ile Leu Glu Asp Trp Asn Phe Gly Leu Gln Pro Pro Pro Gly Gly Thr
385                 390                 395                 400

Leu Glu Asp Thr Tyr Arg Phe Val Thr Ser Gln Ala Ile Ala Cys Gln
                405                 410                 415

Lys His Thr Pro Pro Ala Pro Lys Glu Asp Pro Leu Lys Lys Tyr Thr
            420                 425                 430

Phe Trp Glu Val Asn Leu Lys Glu Lys Phe Ser Ala Asp Leu Asp Gln
        435                 440                 445

Phe Pro Leu Gly Arg Lys Phe Leu Leu Gln Ala Gly Leu Lys Ala Lys
    450                 455                 460

Pro Lys Phe Thr Leu Gly Lys Arg Lys Ala Thr Pro Thr Thr Ser Ser
465                 470                 475                 480
```

```
Thr Ser Thr Thr Ala Lys Arg Lys Lys Arg Lys Leu
                485                 490


<210> SEQ ID NO 8
<211> LENGTH: 1512
<212> TYPE: DNA
<213> ORGANISM: Artificial sequence
<220> FEATURE:
<223> OTHER INFORMATION: Synthesized in the laboratory

<400> SEQUENCE: 8

catatgcttc ctagtgaggc cactgtctac ttgcctcctg tcccagtatc taaggttgta     60

agcacggatg aatatgttgc acgcacaaac atatattatc atgcaggaac atccagacta    120

cttgcagttg gacatcccta ttttcctatt aaaaaaccta acaataacaa aatattagtt    180

cctaaagtat caggattaca atacagggta tttagaatac atttacctga ccccaataag    240

tttggttttc ctgacacctc attttataat ccagatacac agcggctggt ttgggcctgt    300

gtaggtgttg aggtaggtcg tggtcagcca ttaggtgtgg gcattagtgg ccatccttta    360

ttaaataaat tggatgacac agaaaatgct agtgcttatg cagcaaatgc aggtgtggat    420

aatagagaat gtatatctat ggattacaaa caaacacaat tgtgtttaat tggttgcaaa    480

ccacctatag gggaacactg gggcaaagga tccccatgta ccaatgttgc agtaaatcca    540

ggtgattgtc caccattaga gttaataaac acagttattc aggatggtga tatggttgat    600

actggctttg gtgctatgga ctttactaca ttacaggcta acaaaagtga agttccactg    660

gatatttgta catctatttg caaatatcca gattatatta aaatggtgtc agaaccatat    720

ggcgacagct tatttttta tctacgaagg gaacaaatgt ttgttagaca tttatttaat    780

agggctggtg ctgttggtga taatgtacca gacgatttat acattaaagg ctctgggtct    840

actgcaaatt tagccagttc aaattatttt cctacaccta gtggttctat ggttacctct    900

gatgcccaaa tattcaataa accttactgg ttacaacgag cacagggcca caataatggc    960

atttgttggg gtaaccaact atttgttact gttgttgata ctacacgcag tacaaatatg   1020

tcattatgtg ctgccatatc tacttcagaa actacatata aaaatactaa ctttaaggag   1080

tacctacgac atggggagga atatgattta cagtttattt ttcaactgtg caaaataacc   1140

ttaactgcag acattatgac atacatacat tctatgaatt ccactatttt ggaggactgg   1200

aattttggtc tacaacctcc cccaggaggc acactagaag atacttatag gtttgtaaca   1260

tcccaggcaa ttgcttgtca aaaacataca cctccagcac ctaaagaaga tccccttaaa   1320

aaatacactt tttgggaagt aaatttaaag gaaaagtttt ctgcagacct agatcagttt   1380

cctttaggac gcaaattttt actacaagca ggattggagg ccaaaccaaa atttacatta   1440

ggaaaacgaa aagctacacc caccacctca tctacctcta caactgctaa acgcaaaaaa   1500

cgtaagctgt aa                                                       1512


<210> SEQ ID NO 9
<211> LENGTH: 504
<212> TYPE: PRT
<213> ORGANISM: Artificial sequence
<220> FEATURE:
<223> OTHER INFORMATION: Synthesized in the laboratory

<400> SEQUENCE: 9

Met Arg Pro Ser Asp Asn Thr Val Tyr Leu Pro Pro Pro Ser Val Ala
1               5                   10                  15

Arg Val Val Asn Thr Asp Asp Tyr Val Thr Arg Thr Ser Ile Phe Tyr
```

```
            20                  25                  30

His Ala Gly Ser Ser Arg Leu Leu Thr Val Gly Asn Pro Tyr Phe Arg
        35                  40                  45

Val Pro Ala Gly Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
        355                 360                 365

Asp Leu Gln Phe Ile Phe Gln Leu Cys Thr Ile Thr Leu Thr Ala Asp
    370                 375                 380

Val Met Ser Tyr Ile His Ser Met Asn Ser Ser Ile Leu Glu Asp Trp
385                 390                 395                 400

Asn Phe Gly Val Pro Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
        435                 440                 445
```

```
Leu Lys Glu Lys Phe Ser Leu Asp Leu Asp Gln Tyr Pro Leu Gly Arg
    450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500


<210> SEQ ID NO 10
<211> LENGTH: 496
<212> TYPE: PRT
<213> ORGANISM: Artificial sequence
<220> FEATURE:
<223> OTHER INFORMATION: Synthesized in the laboratory

<400> SEQUENCE: 10

Met Asp Ser Thr Val Tyr Val Pro Pro Pro Asn Pro Val Ser Lys Val
1               5                   10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
        35                  40                  45

Arg Ala Asn Lys Thr Val Val Pro Lys Val Ser Gly Tyr Gln Tyr Arg
    50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
            100                 105                 110

His Pro Phe Leu Asn Lys Tyr Asp Asp Val Glu Asn Ser Gly Ser Gly
        115                 120                 125

Gly Asn Pro Gly Gln Asp Asn Arg Val Asn Val Gly Met Asp Tyr Lys
    130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
        195                 200                 205

Lys Ser Asp Val Pro Ile Asp Ile Cys Gly Thr Thr Cys Lys Tyr Pro
    210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
        275                 280                 285

Gly Ser Leu Val Ser Ser Glu Ala Gln Leu Phe Asn Lys Pro Tyr Trp
    290                 295                 300
```

```
Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
            340                 345                 350

Glu Tyr Met Arg His Val Glu Glu Tyr Asp Leu Gln Phe Ile Phe Gln
        355                 360                 365

Leu Cys Ser Ile Thr Leu Ser Ala Glu Val Val Ala Tyr Ile His Thr
    370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
        435                 440                 445

Glu Leu Asp Gln Tyr Pro Leu Gly Arg Lys Phe Leu Leu Gln Ser Gly
    450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495


<210> SEQ ID NO 11
<211> LENGTH: 498
<212> TYPE: PRT
<213> ORGANISM: Artificial sequence
<220> FEATURE:
<223> OTHER INFORMATION: Synthesized in the laboratory

<400> SEQUENCE: 11

Met Ser Asp Ser Thr Val Tyr Val Pro Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175
```

```
Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys
```

<210> SEQ ID NO 12
<211> LENGTH: 20
<212> TYPE: DNA
<213> ORGANISM: Artificial sequence
<220> FEATURE:
<223> OTHER INFORMATION: Synthesized in the laboratory

<400> SEQUENCE: 12
tatagttcca gggtctccac 20

<210> SEQ ID NO 13
<211> LENGTH: 22
<212> TYPE: DNA

```
<213> ORGANISM: Artificial sequence
<220> FEATURE:
<223> OTHER INFORMATION: Synthesized in the laboratory

<400> SEQUENCE: 13

acaacaaaca acactaattc aa                                          22


<210> SEQ ID NO 14
<211> LENGTH: 33
<212> TYPE: DNA
<213> ORGANISM: Artificial Sequence
<220> FEATURE:
<223> OTHER INFORMATION: Synthesized in the laboratory

<400> SEQUENCE: 14

ggatcccata tgcttcctag tgaggccact gtc                              33


<210> SEQ ID NO 15
<211> LENGTH: 26
<212> TYPE: DNA
<213> ORGANISM: Artificial Sequence
<220> FEATURE:
<223> OTHER INFORMATION: Synthesized in the laboratory

<400> SEQUENCE: 15

ctcgagttac agcttacgtt ttttgc                                      26
```

TRUNCATED L1 PROTEIN OF HUMAN PAPILLOMAVIRUS TYPE 16

FIELD OF THE INVENTION

The invention relates to a truncated L1 protein of the Human Papillomavirus Type 16, a virus-like particle (VLP) consisting of the protein, a vaccine comprising said virus-like particle, and the use of the vaccine in the prevention of cervical cancer.

BACKGROUND OF THE INVENTION

The human papillomavirus, a non-enveloped, deoxyribonucleic acid (DNA) virus, belongs to the genus of papovaviridae. The viral genome is a double-stranded, closed circle DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. Viral particles are 45-55 nm in diameter, wherein the nucleocapsid, consisting of L1 and L2, exhibits icosahedral symmetry and comprise 72 capsomers.

Currently, there are over 90 different types of HPV, mainly causing papillary disease in the skin and mucosa of human. HPV types are divided into three groups depending on their relation with tumorigenesis: (1) group of low or no cancerogenic risk, containing types 6, 11, 39, 41, 42, and 43; (2) group of medium cancerogenic risk, containing types 31, 33, 35, 51, and 52; and (3) group of high cancerogenic risk, containing types 16, 18, 45, and 58.

Molecular epidemiological investigation suggests that infection by high-risk HPV types is a principle factor in the development of cervical cancer. HPV DNA is detected in over 80% of cervical cancer cases, with about 60% for HPV16 and another 25-30% for other high-risk types such as HPV 18, 31, 45, and 58 (Clifford, G, S. Franceschi, et al. Vaccine 2006. 24 Suppl 3:S26-34).

Cervical cancer is the second most common malignant tumor among women, following breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total, and about 15% of these involve malignant neoplasms, in contrast to 1.5% in developed countries. Cervical cancer is most prevalent in sub-Saharan Africa, Latin America, and Southern and Eastern Asia. Cervical cancer is also prevalent in China. The incidence of cervical cancer among married women is as high as 1026/100000 in Lueyang County of Shanxi Province. Therefore, a safe and effective HPV vaccine, especially against high-risk types such as HPV 16 and 18, would be an effective way to prevent cervical cancer and improve health of women.

HPV L1 protein, with a molecular weight of 55-60 kDa, is the major capsid protein of the human papillomavirus and the main target protein of the HPV vaccine. HPV L1 protein expressed in multiple different expression systems can form Virus-like particles (VLPs) which resemble native HPV particles morphologically, without the assistance of the L2 protein. The VLP, consisting of 72 pentamers of the L1 proteins, exhibits icosahedral symmetry. Since the VLPs retain the native epitopes of the viral particles, they are highly immunogenic and can induce the generation of neutralizing antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral DNA. Therefore, VLP vaccines become the primary candidate for an HPV vaccine.

The key for development of a vaccine is to efficiently produce VLP vaccines of HPV in large-scale. Currently, the most commonly used expression systems are eukaryotic expression systems and prokaryotic expression systems.

The commonly used eukaryotic systems comprise poxvirus, insect baculovirus and yeast vectors. HPV L1 protein expressed in eukaryotic systems shows little conformational difference from that of the native virus, and can self-assemble into VLPs. Thus, purified VLPs can be easily obtained after gradient density centrifugation. It brings a lot of convenience to the purification work. However, due to the high culture costs and low expression level, it is quite difficult to product industrially on a large-scale. The HPV vaccine Gardasil®, which came into the market recently, is more expensive than others due to low expression level and high production cost of the *Saccharomyces cerevisiae* expression system employed in its manufacture.

The expression of HPV L1 protein in a prokaryotic system such as *E. coli* has been previously reported. Banks, Matlashewski, et al. published a paper regarding the expression of HPV 16 L1 by employing *E. coli* (Banks, L., G. Matlashewski, et al. (1987). J Gen Virol 68 (Pt 12): 3081-9). However, most HPV L1 proteins expressed by *E. coli* lose their native conformation and cannot induce the generation of protective antibodies against HPV. Alternatively, although HPV VLPs can be obtained from the incorrectly folded proteins by steps such as purification from inclusion bodies and refolding, it is difficult to apply this method to production in large-scale, as the protein is largely lost during the refolding process and the yield is low (Kelsall, S. R. and J. K. Kulski (1995). J Virol Methods 53(1): 75-90). Although HPV L1 protein may be expressed in a soluble form with a correct conformation in *E. coli* and dissolved in the supernatants of *E. coli* lysate, the expression level is low. Moreover, since there are large number and amount of impure proteins, it is difficult to isolate the proteins of interest from them. Although it is reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to production on a larger scale because expensive enzymes are required to cleave the fusion protein.

Therefore, a HPV L1 protein capable of inducing the generation of protective antibodies against HPV, and a virus-like particle consisting of the same are still needed in the art, so that it is possible to produce vaccines for cervical cancer industrially on a large scale.

DESCRIPTION OF THE INVENTION

This invention aims to provide a novel HPV type 16 L1 protein, the VLPs consisting of it, and a vaccine comprising the VLPs.

During research, it was found by chance that the *E. coli* expression system can produce a truncated HPV 16 L1 protein that can induce the generation of neutralizing antibodies against HPV 16. After purification, the truncated HPV16 L1 protein can be produced in high yield, with at least 50% purity. Further treatment of the purified HPV16 L1 protein can produce VLPs, which can induce the production of neutralizing antibodies. The invention has been completed based on the above.

Therefore, the first aspect of the invention relates to HPV 16 L1 proteins with 4, 6, 8, 10, 20, 30 or 40 amino acids truncated at N-terminal as compared to a wild type HPV 16 L1 protein. Preferably, the truncated protein has the sequence set forth in SEQ ID Nos:1, 2, 3, 4, 5, 6, or 7, especially the sequence set forth in SEQ ID NO:6.

A further aspect of the invention relates to a polynucleotide encoding the truncated protein according to the invention, and a vector containing the polynucleotide.

A further aspect of the invention relates to a cell comprising the vector.

The invention also relates to a composition comprising the truncated protein, the polynucleotide, the vector, or the cell.

A further aspect of the invention relates to a HPV 16 VLP, comprising or consisting of HPV 16 L1 proteins with 4, 6, 8, 10, 20, 30 or 40 amino acids truncated at the N terminal such as HPV 16 L1 proteins having a sequence set forth in SEQ ID NOs: 1, 2, 3, 4, 5, 6, or 7.

A further aspect of the invention relates to a method of obtaining HPV 16 L1 protein, comprising the expression of a truncated HPV 16 L1 gene fragment in an *E. coli* expression system and the subsequent purification of the protein from the lysate supernatant.

In a preferred embodiment of the invention, a method of obtaining HPV 16 L1 protein comprises:

a) expressing a truncated HPV 16 L1 gene fragment in a *E. coli* expression system;

b) disrupting the *E. coli*, which has expressed the truncated HPV 16 L1 protein, in a salt solution at a concentration of from 100 mM to 600 mM, and isolate the supernatant;

c) decreasing the salt concentration of the supernatant in b) to from 100 mM to 0, inclusive, by using water or a low salt solution, and collecting a precipitate;

d) redissolving the precipitation in c) in a salt solution at a concentration of from 150 mM to 2500 mM, with a reductant added, and then isolating the resultant solution, wherein the solution contains the truncated HPV 16 L1 protein with a purity of at least 50%.

More generally, the invention also relates to a method of obtaining a HPV L1 protein, such as the HPV 16 L1 protein according to the invention, comprising:

a) expressing the HPV L1 gene encoding HPV L1 protein in an *E. coli* expression system;
b) disrupting *E. coli*, which has expressed the truncated HPV L1 protein, in a salt solution at a concentration of from 100 mM to 600 mM, and isolating the supernatant;
c) decreasing the salt concentration of the supernatant in b) to from 100 mM to 0, inclusive, by using water or a low salt solution, and collecting a precipitate;
d) redissolving the precipitation in c) in a salt solution at a concentration of from 150 mM to 2500 mM, with a reductant added, and then isolating the resultant solution, wherein the solution contains the truncated HPV L1 protein with a purity of at least 50%.

The invention also relates to a vaccine for the prevention of cervical cancer, comprising VLPs of HPV 16 L1 proteins according to the invention, preferably in an amount effective to prevent cervical cancer. Preferably, the vaccine further comprises at least one VLP of HPV18, 11, 6, 31, 33, 45, 52, or 58 L1 proteins, preferably in an amount effective to prevent cervical cancer or infection caused by the corresponding HPV types. Generally, the vaccine further contains excipients or vectors for vaccine.

Preferably, the vaccine comprises HPV 16 VLPs and HPV 18 VLPs, especially the HPV 16 VLPs comprising or consisting of the protein having the amino acid sequence set forth in SEQ ID No: 6, and the HPV 18 VLPs comprising or consisting of the protein having the amino acid sequence set forth in SEQ ID No: 9. More preferably, the vaccine further comprises HPV 6 VLPs and HPV 11 VLPs, especially the HPV 6 VLPs comprising or consisting of the protein having the amino acid sequence set forth in SEQ ID No: 10, and the HPV 11 VLPs comprising or consisting of the protein having the amino acid sequence set forth in SEQ ID No: 11.

In a specially preferred embodiment, the vaccine comprises the HPV 16 VLPs comprising or consisting of the protein having the amino acid sequence set forth in SEQ ID No: 6, the HPV 18 VLPs comprising or consisting of the protein having the amino acid sequence set forth in SEQ ID No: 9, the HPV 6 VLPs comprising or consisting of the protein having the amino acid sequence set forth in SEQ ID No: 10, and the HPV 11 VLPs comprising or consisting of the protein having the amino acid sequence set forth in SEQ ID No: 11, preferably, in an amount effective to prevent cervical cancer or infection caused by the corresponding HPV subtypes.

The invention further relates to the use of the HPV 16 L1 protein or the VLPs thereof in the manufacture of a vaccine for the prevention of cervical cancer.

The invention further relates to a method of preventing cervical cancer, comprising administrating a vaccine comprising a preventively effective amount of HPV 16 L1 protein to an individual in need of it.

The invention involves a method for obtaining VLPs of the HPV 16 L1 protein, comprising:

e) further purifying the truncated HPV 16 L1 protein with a purity of at least 50% by subjecting it to a chromatography;
f) removing the reductant from the HPV 16 L1 protein obtained in e).

This invention involves a method of preparing a vaccine for preventing cervical cancer, comprising blending the VLPs above, and optionally, one or more VLPs selected from the group consisting of VLPs of HPV types 6, 11, 18, 31, 33, 45, 52, and 58, and vectors or excipients for vaccines.

DEFINITIONS OF THE TERM IN PRESENT INVENTION

According to the invention, the term "*E. coli* expression system" refers to a expression system consisting of *E. coli* (strains) and vectors, wherein the *E. coli* (strains) include, but are not limited to: ER2566, BL21 (DE3), B834 (DE3), and BLR (DE3), which are available on the market.

According to the invention, the term "vectors" refers to the nucleic acid carrier tools which have the polynucleotide encoding a certain protein inserted therein and allow for the expression of the protein. The "vector" can have the carried genetic material expressed in a host cell by transformation, transduction, and transfection into the host cell. For example, "vectors" include plasmids, phages, cosmids and the like.

According to the invention, the term "a gene fragment of the truncated HPV 16 L1 protein" refers to the nucleic acids with the nucleotide(s) encoding one or more amino acid sequences deleted at 5' or 3' terminal of the wild-type HPV 16 L1 gene (cDNA). The full-length gene sequence of the wild-type HPV 16 L1 gene can be found in, but not limited to, the following NCBI sequences: AY686583.1, DQ469930.1, DQ155283.1 and AF393502.1.

The term "truncated HPV 16 L1 protein" refers to the protein with one or more amino acids deleted at the N- and/or C-terminal of the wild-type HPV 16 L1 protein. The full-length gene sequence of the wild-type HPV 16 L1 protein can be found in, but not limited to, the full-length L1 proteins encoded by the following NCBI sequences: AY686583.1, DQ469930.1, DQ155283.1 and AF393502.1.

According to the invention, the term "excipients and vectors for vaccines" refers to one or more reagents, including but not limited to: pH regulators, surfactants, adjuvants, and ionic strength enhancers. For example, pH regulators include, but are not limited to, phosphate buffers; surfactants include, but are not limited to: anion surfactants, cation surfactants, non-ionic surfactants (for example, but not limited to Tween-80); adjuvants include, but are not limited to, aluminum hydroxide and Freund's complete adjuvant; and Ionic strength enhancers include, but are not limited to, NaCl.

According to the invention, the term "chromatography" includes, but is not limited to: ion exchange chromatography (e.g. cation-exchange chromatography), hydrophobic interaction chromatography, absorbant chromatography (e.g. hydroxyapatite chromatography), gel filtrate chromatography (gel exclusion chromatography), and affinity chromatography.

According to the invention, the truncated HPV 16 L1 proteins can be obtained preferably by the following steps:

a) disrupting *E. coli*, which expresses truncated HPV 16 L1 protein, in a buffer containing 100-600 mM salt, preferably 200-500 mM;
b) isolating the supernatant from the disrupted solution, then decreasing the salt concentration of the supernatant to 100 mM-0M with water or a low-salt buffer (generally, with a salt concentration lower than the one of the buffer for disrupting);
c) separating a precipitant from the supernatant with a salt concentration as low as 100 mM-0;
d) redissolving the precipitant in a solution containing a reductant and having a salt concentration of 150-2000 mM, preferably greater than 200 mM;
e) isolating a solution of the truncated HPV 16 L1 proteins with a purity of at least 50%, preferably at least 70%, more preferably at least 80%.

According to the invention, in the method for obtaining the truncated HPV 16 L1 proteins, the term "buffer" refers to a solution which can maintain pH value stable within a certain range, including but not limited to: Tris buffers, phosphate buffers, HEPES buffers, and MOPS buffers.

According to the invention, the disrupting of the prokaryotic host cell can be achieved by methods including, but not limited to one or more of homogenizer disrupting, ultrasonic treatment, grinding, high pressure extrusion, and lysozyme treatment.

According to the invention, in the method for obtaining the truncated HPV 16 L1 proteins, the salts used include, but are not limited to: one or more of neutral salts, especially alkali metal salt, ammonium salts, hydrochlorides, sulfates, bicarbonates, phosphate salts or hydrogenphosphates, especially NaCl, KCl, $NH_4Cl$, $(NH_4)_2SO_4$. NaCl is preferred. The reductant used includes, but is not limited to, DTT and 2-mercaptoethanol, in an amount of including, but not limited to, 10-100 mM.

According to the invention, the VLPs of the truncated HPV 16 L1 protein can be produced by the following steps: further purifying the truncated HPV 16 L1 protein with a purity of at least 50% by subjecting it to a chromatography, and thereby obtaining a purified truncated HPV 16 L1 protein solution; and removing the reductant from the purified HPV 16 L1 protein solution, and thereby obtaining the truncated HPV 16 L1 VLPs. Methods for removing the reductant include, but are not limited to, known techniques in the art, such as dialysis, ultrafiltration, and chromatography.

According to the invention, the truncated HPV L1 protein preferably has the sequence set forth in SEQ ID NO:6.

According to the invention, the vaccine can be administrated in a patient-accepted form, including but not limited to oral and injection, preferably injection.

According to the invention, the vaccine is preferably used in a unit dose. Each unit dose contains 5-80 μg truncated HPV 16 L1 VLP, preferably 20-40 μg.

Beneficial Effect

Presently, the expression systems useful for preparing HPV VLPs include eukaryotic and prokaryotic expression systems.

HPV L1 proteins expressed in eukaryotic expression systems retain their native conformation, and can form VLPs on their own. In most cases, VLP with a correct conformation can be obtained by simple purification. Nevertheless, eukaryotic expression systems, such as the baculovirus and yeast expression systems, are difficult to be applied in large-scale industrial production due to low expression levels and high costs.

Prokaryotic expression systems, such as *E. coli* systems, have the advantages of high expression levels at a lower cost. However, when expressed in a prokaryotic system, the HPV L1 protein usually loses its native conformation and is expressed in a form of inclusion bodies in the precipitant. Renaturation of the protein from inclusion bodies is still a problem worldwide. Due to the difficulty and inefficiency of renaturation, this method is limited to small-scale lab research and cannot be applied on a large scale so as to obtain VLP with a correct conformation from the inclusive bodies. Although the HPV L1 protein can exist in its native conformation in the supernatant of *E. coli* lysate, its expression levels are low. Moreover, it is quite difficult to purify the HPV L1 protein from the numerous soluble proteins in the *E. coli* lysate supernatant. Generally, the purification is completed by means such as fusion expression and affinity chromatography which are not feasible for industrial-scale processes due to expensive enzymes employed therein.

In this invention, N-truncated HPV 16 L1 protein is expressed in an *E. coli* expression system and is selectively precipitated from the *E. coli* lysate supernatant under mild conditions. The HPV16 L1 protein is then redissolved in a salt buffer to significantly improve its purity while still retaining its native conformation. The redissolved protein of interest can be immediately subjected to ion-exchange or hydrophobic interaction chromatography so as to obtain the pure protein. The purified, truncated HPV 16 L1 protein obtained from these steps, can self-assemble into VLPs with good immunogenicity and the ability to induce neutralizing antibodies of a high titer against HPV 16, which is a good vaccine for preventing human from HPV 16 infection. In addition, the truncated HPV 16 L1 protein used in the present invention is easily expressed in an *E. coli* expression system and can be economically purified without using expensive enzymes. Furthermore, because the protein of interest is not subjected to the intensive procedures of denaturation and renaturation during purification, the method can be applied industrially on a large scale due to low loss.

These and other aspects of the invention will be more apparent after referring to the following detailed description and the drawings. All public references are hereby incorporated by reference in their entirety.

FIGURE DESCRIPTIONS

FIG. 1 shows the SDS-PAGE result of HPV16N30C-L1 protein in different steps of Example 2 according to the invention. M: Molecular Weight Marker; Lane 1: Lysate supernatant; Lane 2: Precipitation following desalinating dialysis; Lane 3: precipitation after re-suspension; Lane 4: the supernatant after re-suspension. The result shows that the purity of HPV16N30C-L1 increased from about 10% to about 70% following the steps of precipitation and re-dissolution.

FIG. 2 shows the SDS-PAGE result of HPV16N30C-L1 purified by HIC (Hydrophobic Interaction Chromatography) in Example 3. Lane 1: HPV16N30C-L1 before loading on the butyl column; Lanes 2 and 3: HPV16N30C-L1 passing through the butyl column; Lanes 4 and 5: HPV16N30C-L1 eluted with 1M NaCl; Lane 6: HPV16N30C-L1 eluted with 800 mM NaCl; Lane 7: HPV16N30C-L1 eluted with 500 mM NaCl. After the purification by Butyl Sepharose 4 Fast Flow Hydrophobic column, the purity of HPV 16 L1 protein eluted with 800 mM NaCl and 500 mM NaCl reaches above 98%.

Figure 5:
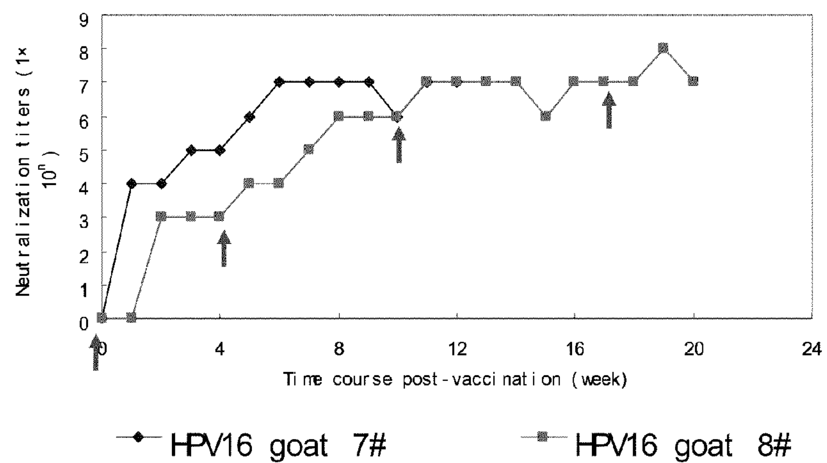

FIG. 5: shows titers of neutralizing antibodies in serum at different stages after inoculation of goat with HPV16N30C-L1 VLPs obtained in Example 5. Vaccination times are indicated with arrows. The titer of neutralizing antibodies increased rapidly a week after the first vaccination, and reached a peak level of $10^6$-$10^7$ after a booster.

Figure 6:
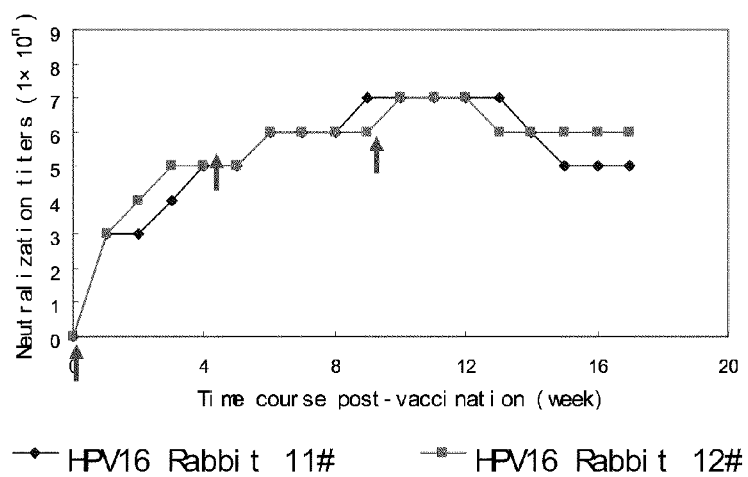

FIG. 6 shows titers of neutralizing antibodies in serum at different stages after inoculation of rabbit with HPV16N30C-L1 VLPs obtained in Example 5. Vaccination times are indicated with arrows. The titer of neutralizing antibodies increased rapidly a week after the first vaccination, and reached a peak level of $10^6$ after a booster.

Figure 7:
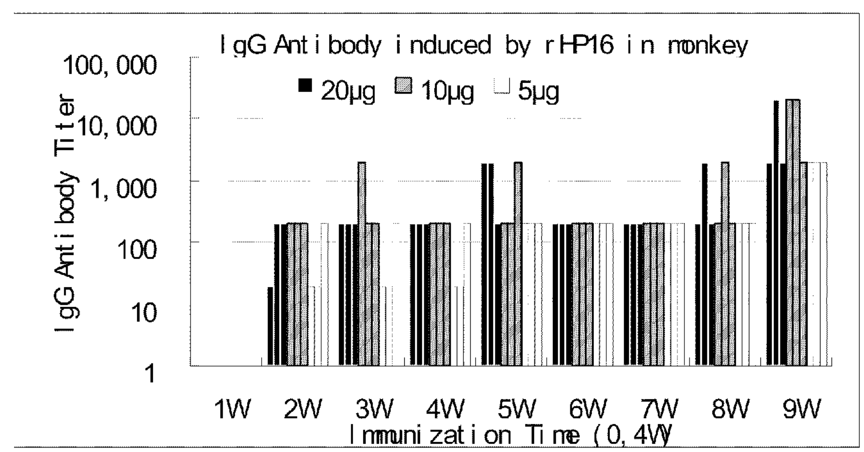

FIG. 7 shows the titers of total immunoglobulin G (IgG) antibody against HPV 16 in serum at different times after inoculation of rhesus monkey with HPV16/18 bivalent vaccine obtained in Example 5. Vaccine was administered at 0 and 4 weeks. The titer of total IgG antibody increased rapidly after the first vaccination, reaching 20,000 times of the original one.

Figure 8:
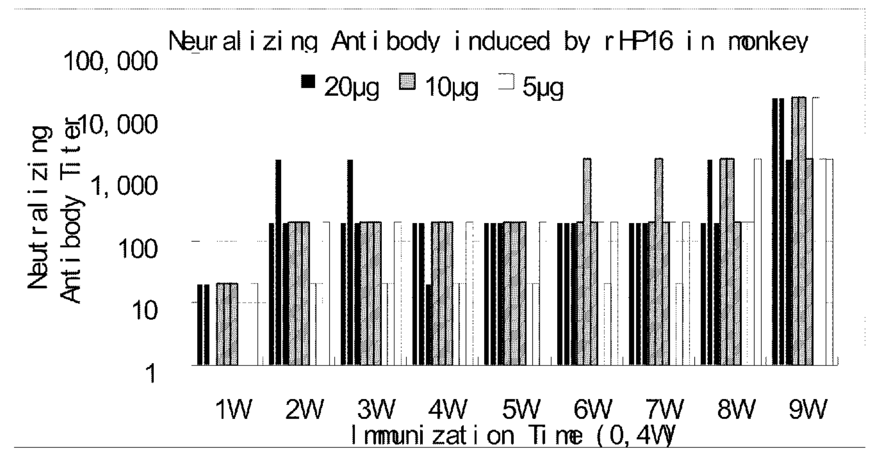

FIG. 8 shows the titers of neutralizing antibodies against HPV 16 in serum at different times after inoculation of rhesus monkey with HPV16/18 bivalent vaccine obtained in Example 5. Vaccine was administered at 0 and 4 weeks. The titer of neutralizing antibody increased rapidly after the first vaccination, reaching 20,000 times of the original one.

Figure 9:
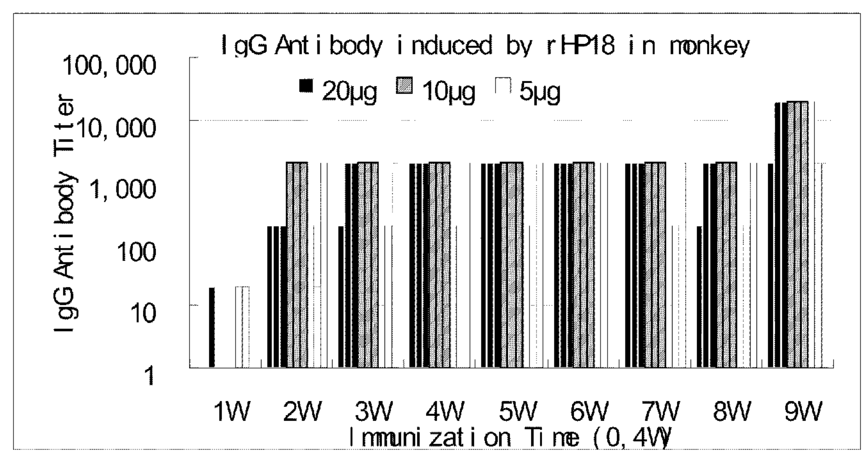

FIG. 9 shows the titers of total immunoglobulin G (IgG) antibody against HPV 18 in serum at different times after inoculation of rhesus monkey with HPV16/18 bivalent vaccine obtained in Example 5. Vaccine was administered at 0 and 4 weeks. The titer of total IgG antibody increased rapidly after the first vaccination, reaching 20,000 times of the original one.

Figure 10:
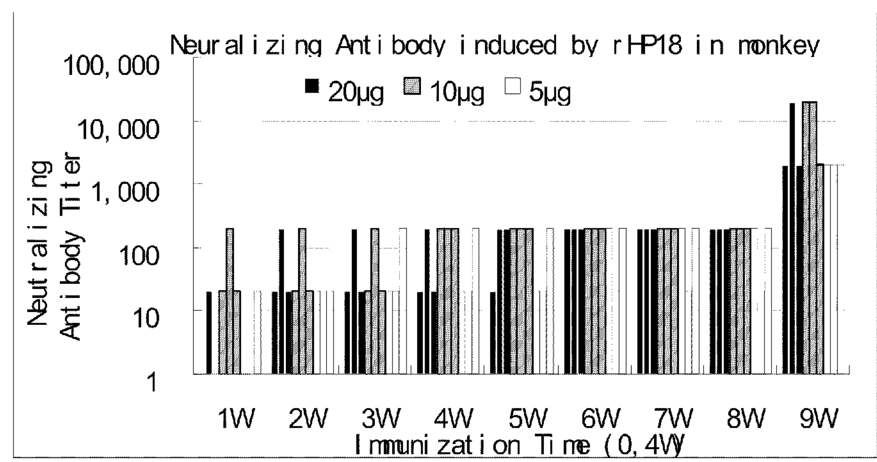

FIG. 10 shows the titers of neutralizing antibodies against HPV 18 in serum at different times after inoculation of rhesus monkey with HPV16/18 bivalent vaccine obtained in Example 5. Vaccine was administered at 0 and 4 weeks. The titer of neutralizing antibody increased rapidly after the first vaccination, reaching 20,000 times of the original one.

Figure 11:
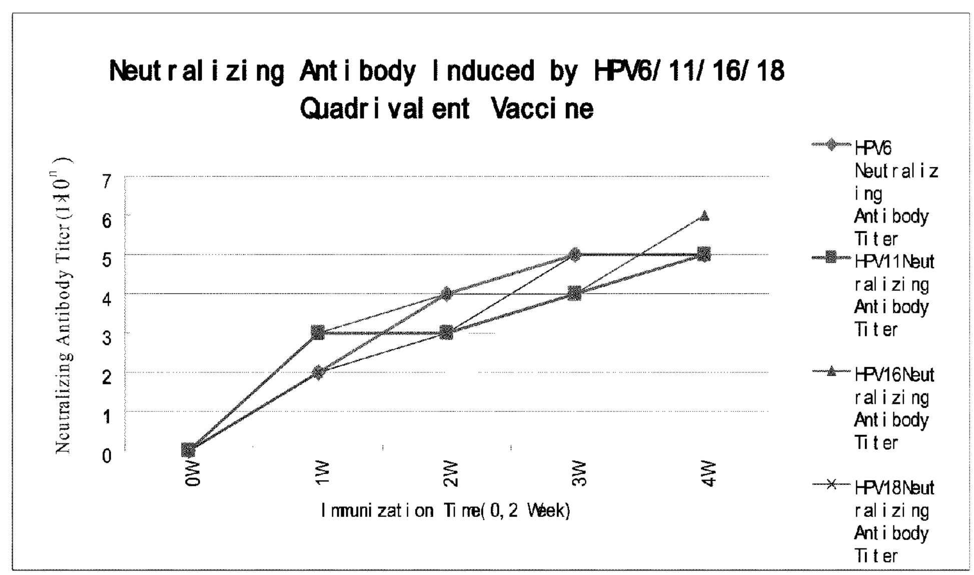

FIG. 11 shows the changes of titers of neutralizing antibodies against HPV6, HPV11, HPV16 and HPV18 after inoculation of mouse with HPV6/11/16/18 quadrivalent vaccine obtained in Example 5. Vaccine was administered at 0 and 2 weeks. The titers of neutralizing antibodies against HPV6, HPV11, HPV16 and HPV18 increased rapidly after the first vaccination, reaching $10^5$-$10^6$ after a booster.

SEQUENCE LIST

SEQ1 (SEQ ID NO: 1):

```
  1 MFIYILVITC YENDVNVYHI FFQMSLWLPS EATVYLPPVP VSKVVSTDEY VARTNIYYHA
 61 GTSRLLAVGH PYFPIKKPNN NKILVPKVSG LQYRVFRIHL PDPNKFGFPD TSFYNPDTQR
121 LVWACVGVEV GRGQPLGVGI SGHPLLNKLD DTENASAYAA NAGVDNRECI SMDYKQTQLC
181 LIGCKPPIGE HWGKGSPCTN VAVNPGDCPP LELINTYIQD GDMVDTGFGA MDFTTLQANK
241 SEVPLDICTS ICKYPDYIKM VSEPYGDSLF FYLRREQMFV RHLFNRAGAV GDNVPDDLYI
301 KGSGSTANLA SSNYFPTPSG SMVTSDAQIF NKPYWLQRAQ GHNNGICWGN QLFVTVVDTT
361 RSTNMSLCAA ISTSETTYKN TNFKEYLRHG EEYDLQFIFQ LCKITLTADI MTYIHSMNST
421 ILEDWNFGLQ PPPGGTLEDT YRFVTSQAIA CQKHTPPAPK EDPLKKYTFW EVNLKEKFSA
481 DLDQFPLGRK FLLQAGLEAK PKFTLGKRKA TPTTSSTSTT AKRKKRKL
```

SEQ2 (SEQ ID NO: 2):

```
  1 MYILVITCYE NDVNVYHIFF QMSLWLPSEA TVYLPPVPVS KVVSTDEYVA RTNIYYHAGT
 61 SRLLAVGHPY FPIKKPNNNK ILVPKVSGLQ YRVFRIHLPD PNKFGFPDTS FYNPDTQRLV
121 WACVGVEVGR GQPLCVGISG HPLLNKLDDT ENASAYAANA GVDNRECISM DYKQTQLCLI
181 GCKPPIGEHW GKGSPCTNVA VNPGDCPPLE LINTVIQDGD MVDTGFGAMD FTTLQANKSE
241 VPLDICTSIC KYPDYIKMVS EPYGDSLFFY LRREQMFVRH LFNRAGAVGD NVPDDLYIKG
301 SGSTANLASS NYFPTPSGSM VTSDAQIFNK PYWLQRAQGH NNGICWGNQL FVTVVDTTRS
361 TNMSLCAAIS TSETTYKNTN FKEYLRHGEE YDLQFIFQLC KITLTADIMT YIHSMNSTIL
```

-continued

SEQUENCE LIST

```
421 EDWNFGLQPP PGGTLEDTYR FVTSQAIACQ KHTPPAPKED PLKKYTFWEV NLKEKFSADL
481 DQFPLGRKFL LQAGLEAKPK FTLGKRKATP TTSSTSTTAK RKKRKL
```

SEQ3 (SEQ ID NO: 3):

```
  1 MLVITCYEND VNVYHIFFQM SLWLPSEATV YLPPVPVSKV VSTDEYVART NIYYHAGTSR
 61 LLAVGHPYFP IKKPNNNKIL VPKVSGLQYR VFRIHLPDPN KFGFPDTSFY NPDTQRLVWA
121 CVGVEVGRGQ PLGVGISGHP LLNKLIDTEN ASAYAANAGV DNRECISMDY KQTQLCLIGC
181 KPPIGEHWGK GSPCTNVAVN PGDCPPLELI NTVIQDGDMV DTGFGAMDFT TLQANKSEVP
241 LDICTSICKY PDYIKMVSEP YGDSLFFYLR REQMFVRHLF NRAGAVGDNV PDDLYIKGSG
301 STANLASSNY FPTPSGSMVT SDAQIFNKPY WLQRAQGHNN GICWGNQLFV TVVDTTRSTN
361 MSLCAAISTS ETTYKNTNFK EYLRHGEEYD LQFIFQLCKI TLTADIMTYI HSMNSTILED
421 WNFGLQPPPG GTLEDTYRFV TSQAIACQKH TPPAPKEDPL KKYTFWEVNL KEKFSADLDQ
481 FPLGRKFLLQ AGLEAKPKFT LGKRKATPTT SSTSTTAKRK KRKL
```

SEQ4 (SEQ ID NO: 4):

```
  1 MITCYENDVN VYHIFFQMSL WLPSEATVYL PPVPVSKVVS TDEYVARTNI YYHAGTSRLL
 61 AVGHPYFPIK KPNNNKILVP KVSGLQYRYF RIHLPDPNKF GFPDTSFYNP DTQRLVWACV
121 GVEVGRGQPL GVGISGHPLL NKLDDTENAS AYAANAGVDN RECISMDYKQ TQLCLIGCKP
181 PIGEHWGKGS PCTNVAVNPG DCPPLELINT VIQDGDMVDT GFGAMDFTTL QANKSEVPLD
241 ICTSICKYPD YIKMVSEPYG DSLFFYLRRE QMFVRHLFNR AGAVGDNVPD DLYIKGSGST
301 ANLASSNYFP TPSGSMVTSD AQIFNKPYWL QRAQGHNNGI CWGNQLFVTV VDTTRSTNMS
361 LCAAISTSET TYKNTNFKEY LRHGEEYDLQ FIFQLCKITL TADIMTYIHS MNSTILEDWN
421 FGLQPPPGGT LEDTYRFVTS QAIACQKHTP PAPKEDPLIK YTFWEVNLKE KFSADLDQFP
481 LGRKFLLQAG LEAKPKFTLG KRKATPTTSS TSTTAKRKKR KL
```

SEQ5 (SEQ ID NO: 5):

```
  1 MYHIFFQMSL WLPSEATVYL PPVPVSKVVS TDEYVARTNI YYHAGTSRLL AVGHPYFPIK
 61 KPNNNKILVP KVSGLQYRVF RIHLPDPNKF GFPDTSFYNP DTQRLVWACV GVEVGRCQPL
121 GVGISGHPLL NKLDDTENAS AYAANAGVDN RECISMDYKQ TQLCLIGCKP PIGEHWGKGS
181 PCTNVAVNPG DCPPLELINT VIQDGDMVDT GFGAMDFTTL QANKSEVPLD ICTSICKYPD
241 YIKMVSEPYG DSLFFYLRRE QMFVRHLFNR AGAVGDNVPD DLYIKGSGST ANLASSNYFP
301 TPSGSMVTSD AQIFNKPYWL QRAQGHNNGI CWGNQLFVTV VDTTRSTNMS LCAAISTSET
361 TYKNTNFKEY LRHGEEYDLQ FIFQLCKITL TADIMTYIHS MNSTILEDWN FGLQPPPGGT
421 LEDTYRFVTS QAIACQKHTP PAPKEDPLKK YTFWEVNLKE KFSADLDQFP LGRKFLLQAG
481 LEAKPKFTLG KRKATPTTSS TSTTAKRKKR KL
```

SEQ6 (SEQ ID NO: 6):

```
  1 MLPSEATVYL PPVPVSKVVS TDEYVARTNI YYHAGTSRLL AVGHPYFPIK KPNNNKILVP
 61 KVSGLQYRVF RIHLPDPNKF GFPDTSFYNP DTQRLVWACV GVEVGRGQPL GVGISGHPLL
121 NKLDDTENAS AYAANAGVDN RECISMDYKQ TQLCLIGCKP PIGEHWGKGS PCTNVAVNPG
181 DCPPLELINT VIQDGDMVDT GFGAMDFTTL QANKSEVPLD ICTSICKYPD YIKMVSEPYG
241 DSLFFYLRRE QMFVRHLFNR AGAVGDNVPD DLYIKGSGST ANLASSNYFP TPSGSMVTSD
301 AQIFNKPYWL QRAQGHNNGI CWGNQLFVTV VDTTRSTNMS LCAAISTSET TYKNTNFKEY
361 LRHGEEYDLQ FIFQLCKITL TADIMTYIHS MNSTILEDWN FGLQPPPGGT LEDTYRFVTS
421 QAIACQKHTP PAPKEDPLKK YTFWEVNLKE KFSADLDQFP LGRKFLLQAG LEAKPKFTLG
481 KRKATPTTSS TSTTAKRKKR KL*
```

SEQ7 (SEQ ID NO: 7):

```
  1 MPVPVSKVVS TDEYVARTNI YYHAGTSRLL AVGHPYFPIK KPNNNKILVP KVSGLQYRVF
 61 RIHLPDPNKF GFPDTSFYNP DTQRLVWACV GVEVGRGQPL GVGISGHPLL NKLDDTENAS
121 AYAANAGVDN RECISMDYKQ TQLCLIGCKP PIGEHWGKGS PCTNVAVNPG DCPPLELINT
181 VIQDGDMVDT GFGAMDFTTL QANKSEVPLD ICTSICKYPD YIKMVSEPYG DSLFFYLRRE
241 QMFVRHLFNR AGAVGENVPD DLYIKGSGST ANLASSNYFP TPSGSMVTSD AQIFNKPYWL
301 QRAQGHNNGI CWGNQLFVTV VDTTRSTNMS LCAAISTSET TYKNTNFKEY LRHGEEYDLQ
361 FIFQLCKITL TADVMTYIHS MNSTILEDWN FGLQPPPGGT LEDTYRFVTS QAIACQKHTP
421 PAPKEDPLKK YTFWEVNLKE KFSADLDQFP LGRKFLLQAG LKAKPKFTLG KRKATPTTSS
481 TSTTAKRKKR KL*
```

SEQ8 (SEQ ID NO: 8):

```
  1 CATATGCTTC CTAGTGAGGC CACTGTCTAC TTGCCTCCTG TCCCAGTATC TAAGGTTGTA
 61 AGCACGGATG AATATGTTGC ACGCACAAAC ATATATTATC ATGCAGGAAC ATCCAGACTA
121 CTTGCAGTTG GACATCCCTA TTTTCCTATT AAAAAACCTA ACAATAACAA AATATTAGTT
181 CCTAAAGTAT CAGGATTACA ATACAGGGTA TTTAGAATAC ATTTACCTGA CCCCAATAAG
241 TTTGGTTTTC CTGACACCTC ATTTTATAAT CCAGATACAC AGCGGCTGGT TTGGGCCTGT
301 GTAGGTGTTG AGGTAGGTCG TGGTCAGCCA TTAGGTGTGG GCATTAGTGG CCATCCTTTA
361 TTAAATAAAT TGGATGACAC AGAAAATGCT AGTGCTTATG CAGCAAATGC AGGTGTGGAT
421 AATAGAGAAT GTATATCTAT GGATTACAAA CAAACACAAT TGTGTTTAAT TGGTTGCAAA
481 CCACCTATAG GGGAACACTG GGGCAAAGGA TCCCCATGTA CCAATGTTGC AGTAAATGCA
541 GGTGATTGTC CACCATTAGA GTTAATAAAC ACAGTTATTC AGGATGGTGA TATGGTTGAT
601 ACTGGCTTTC GTGCTATGGA CTTTACTACA TTACAGGCTA ACAAAAGTGA AGTTCCACTG
661 GATATTTGTA CATCTATTTG CAAATATCCA GATTATATTA AAATGGTGTC AGAACCATAT
```

-continued

| SEQUENCE LIST |
|---|
| 721 GGCGACAGCT TATTTTTTTA TCTACGAAGG GAACAAATGT TTGTTAGACA TTTATTTAAT |
| 781 AGGGCTGGTG CTGTTGGTGA TAATGTACCA GACGATTTAT ACATTAAAGG CTCTGGGTCT |
| 841 ACTGCAAATT TAGCCAGTTC AAATTATTTT CCTACACCTA GTGGTTCTAT GGTTACCTCT |
| 901 GATGCCCAAA TATTCAATAA ACCTTACTGG TTACAACGAG CACAGGGCCA CAATAATGGC |
| 961 ATTTGTTGGG GTAACCAACT ATTTGTTACT GTTGTTGATA CTACACGCAG TACAAATATG |
| 1021 TCATTATGTG CTGCCATATC TACTTCAGAA ACTACATATA AAAATACTAA CTTTAAGGAG |
| 1081 TACCTACGAC ATGGGGAGGA ATATGATTTA CAGTTTATTT TTCAACTGTG CAAAATAACC |
| 1141 TTAACTGCAG ACATTATGAC ATACATACAT TCTATGAATT CCACTATTTT GGAGGACTGG |
| 1201 AATTTTGGTC TACAACCTCC CCCAGGAGGC ACACTAGAAG ATACTTATAG GTTTGTAACA |
| 1261 TCCCAGGCAA TTGCTTGTCA AAAACATACA CCTCCAGCAC CTAAAGAAGA TCCCCTTAAA |
| 1321 AAATACACTT TTTGGGAAGT AAATTTAAAG GAAAAGTTTT CTGCAGACCT AGATCAGTTT |
| 1381 CCTTTAGGAC GCAAATTTTT ACTACAAGCA GGATTGGAGG CCAAACCAAA ATTTACATTA |
| 1441 GGAAAACGAA AAGCTACACC CACCACCTCA TCTACCTCTA CAACTGCTAA ACGCAAAAAA |
| 1501 CGTAAGCTGT AA |

The description is further illustrated in combination with the Examples, wherein it is not limited to the Examples.

EXAMPLE 1

Expression of the Truncated HPV16 μl Protein (SEQ ID NO.6)

Preparation of HPV16 μl Gene Fragments as PCR Template

DNA extracted from the vaginal secretion of cervical cancer patients from Xiamen City in Fujian province was used as a template. Forward primers were 16H5521F: 5'-TAT AGT TCC AGG GTC TCC AC-3' (SEQ ID NO:12) and reverse primers were 16H7190R: 5'-ACA ACA AAC AAC ACT AAT TCA A-3' (SEQ ID NO:13). PCR reaction was performed in a Biometra T3 PCR thermocycler using the following parameters:

| | |
|---|---|
| 94° C. denaturation 5 min | |
| 94° C. denaturation 50 sec | 25 cycles |
| 57° C. annealing 50 sec | |
| 72° C. elongation 2 min | |
| 72° C. elongation 10 min | |

The specific amplification product, about 1.6 kb in length, was used as the template to produce DNA fragments of the truncated HPV16 μl protein in the invention.

Construction of Non-Fusion Expression Vector of Truncated HPV16 L1 Gene DNA fragments (1.6 kb) produced in the previous step were used as the template for the next PCR reaction. Forward primer was 16N30F: 5'-GGA TCC CAT ATG CTT CCT AGT GAG GCC ACT GTC-3' (SEQ ID NO:14), at the 5' terminal of which the restriction endonuclease BamHI and NdeI sites were introduced. The sequence of NdeI site was CAT ATG, wherein the ATG was the initiation codon in *E. coli* system. The reverse primer was 16CR: 5'-CTC GAG TTA CAG CTT ACG TTT TTT GC-3' (SEO ID NO:15), at the 5' terminal of which the restriction endonuclease XhoI site was introduced. PCR reaction was performed in a Biometra T3 PCR thermocycler using the following parameters:

| | |
|---|---|
| 94° C. denaturation 5 min | |
| 94° C. denaturation 50 sec | 25 cycles |
| 57° C. annealing 50 sec | |
| 72° C. elongation 2 min | |
| 72° C. elongation 10 min | |

The DNA fragments, about 1.5 kb in length, were obtained after amplification. The PCR products were linked to the pMD 18-T vector (Takara Biosciences). After digestion with BamHI/HindIII, it was identified that positive colonies, wherein the truncated HPV16 L1 gene was inserted, were obtained, designated as pMD 18-T-1-HPV16N30C-L1.

The nucleotide sequence of interest, which was inserted into the plasmid pMD 18-T-HPV16N30C-L1, was determined as SEQ ID NO: 8 by Shanghai Boya Bio Co. through using M13 +/− primers. SEQ ID NO:8 encodes the amino acid sequence set forth in SEQ ID NO:6 which corresponds to a HPV 16 L1 protein having 30 amino acids truncated at its N-terminal and no amino acid truncated at its C-terminal and was designated as HPV16N30C-L1.

The truncated HPV16N30C-L1 gene fragments were obtained by digesting plasmid pMD 18-T-HPV16N30C-L1 with BamHI/XhoI. The fragments were linked to non-fusion expression vector pTO-T7 digested with NdeI/XhoI (Luo Xinwen et al., Chinese Journal of Biotechnology, 2000, 16: 53-57). After digestion with NdeI/XhoI, it was identified that positive expression colonies, wherein L1 protein gene was inserted, were obtained, designated as pTO-T7-HPV16N30C-L1. 1 μL plasmid pTO-T7-HPV16N30C-L1 (0.15 mg/ml) was used to transform 40 μL competent *E. coli* ER2566 (New England BioLabs) prepared by Calcium chloride method, and then was coated on solid LB medium containing kanmycin (at a final concentration of 25 mg/mL, the same as below). The plates were incubated at 37° C. for about 10-12 h until single colonies could be observed clearly. Single colonies were transferred to a tube containing 4 ml liquid LB medium containing kanmycin. Cultures were incubated in a shaking incubator at 220 rpm for 10 h at 37° C., and then 1 ml bacterial solution was freeze-dried and stored at −70° C.

Expression of HPV16N30C-L1 in Large Scale

*E. coli* transformed with pTO-T7-HPV 16-L1 was taken from the freeze-dried strain at −70° C. and diluted with a little sterile water, and then incubated in 50 mL LB medium containing Kanamycin at 200 rpm and 37° C. for 8 h. Then, the cultures were transferred to ten flasks (5 ml culture per flask), each of which contains 500 mL LB medium, and were incubated in a shaking incubator overnight at 200 rpm and 30° C. The cultures were the starter cultures.

| LB medium: | |
|---|---|
| Peptone: | 10 g |
| Yeast extract: | 5 g |
| NaCl: | 10 g |

The above components were dissolved in 1 L deionized water; the resultant solution was adjusted to pH 7.2 by addition of NaOH, sterilized at 121° C. for 30 minutes and cooled to 50° C.

A 50 L fermenter made by Shanghai Baoxing Biological Ltd was used in large-scale incubation. pH electrode was calibrated. 30 L LB medium was prepared and transferred into the fermenter, sterilized in situ at 121° C. for 30 minutes. Dissolved oxygen electrode was calibrated, wherein the value was determined as 0 before introduction of air after sterilization and as 100% prior to inoculation after introduction of air while stirring at 100 rpm at the beginning.

Preparation of the feed: 20 g peptone and 10 g yeast extract were dissolved in 100 ml deionized water to prepare a mixture of peptone and yeast extract (30%), and 50 g glucose was dissolved in 100 ml deionized water to prepared a glucose solution (50%). The two mixtures were sterilized at 121° C. for 20 min.

On the second day, the starter cultures in the ten flasks (for a total of 5 L) were transferred to the fermenter. At 37° C. and pH 7.0, the dissolved $O_2$ was maintained at >40% by regulating agitation rate or air supply manually.

Flow Feed: 50% glucose and 30% mixture of peptone and yeast extract were mixed at a 2:1 mass ratio.

Flow rates were as follows:

The feeding speed:

1 h: 5%

2 h: 10%

3 h: 20%

4 h: 40%

6 h to the end: 60%

When $OD_{600nm}$ reached about 10.0, the culture temperature was lowered to 25° C. and 4 g IPTG was added to begin induction culture of 4 h. Fermentation was halted when $OD_{600nm}$ reached about 60. The culture was then centrifuged to obtain target strains expressing the HPV16N30C-L1 protein (about 3 kg).

EXAMPLE 2

Preparation HPV16N30C-L1 with a Purity of about 70%

Figure 1:
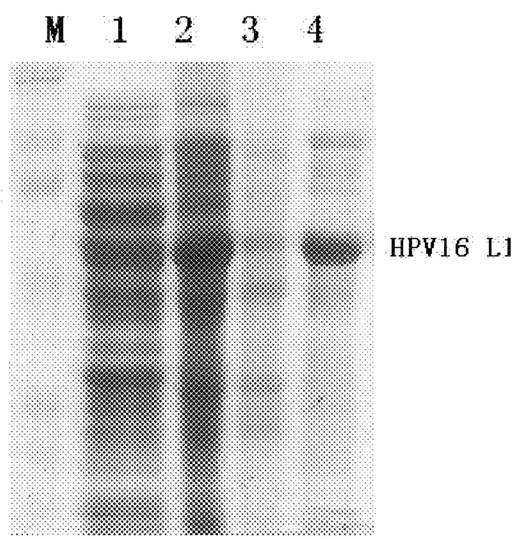

1 g strains were re-suspended in 10 ml lysis buffer (20 mM tris buffer pH 7.2, 300 mM NaCl). Strains were disrupted by passing through a APV homogenizer (Invensys Group) for five times at a pressure of 600 bar. The homogenate was centrifuged at 30,000 g (13,500 rpm in JA-14 rotor) for 15 min. The supernatant was subjected to SDS-PAGE on a 10% gel. At this stage, the HPV16N30C-L1 had a purity of about 10%. The supernatant was dialyzed by a Centrasette 5 Tangential Flow Filter (Pall Co.) running at a pressure of 0.5 psi, a flow rate of 500 ml/min, and a tangential flow rate of 200 mL/min, wherein the retention molecular weight was 30 kDa, the dialysate was 10 mM phosphate buffer pH 6.0, and the dialysis volume was three times as large as the volume of supernatant. After thorough dialysis, the mixture was centrifuged at 12,000 g (9500 rpm in JA-10 rotor (Beckman J25 high speed centrifuge)) for 20 min, and the precipitation was collected. The precipitation was re-suspended in 10 mM phosphate buffer pH 7.5 containing 10 mM DTT and 300 mM NaCl, wherein the volume of the buffer was 1/10 times as large as the volume of the supernatant. The mixture was stirred for 30 min and centrifuged at 30,000 g (13,500 rpm in JA-14 rotor (Beckman J25 high speed centrifuge)) for 20 min. The supernatant passes through a 0.22 μm filter membrane. The sample was further subjected to cation exchange chromatography. 30 μL of 6× loading buffer was added to 150 μL of the filtered supernatant, and the result solution was mixed. After heating in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 1. According to the analysis of SDS-PAGE, HPV16N30C-L1 protein was purified and enriched after the steps of precipitation and re-dissolution, with the purity increased from about 10% to about 70%.

EXAMPLE 3

Chromatography Purification of HPV16N30C-L1

Cation Exchange Chromatography of HPV16N30C-L1

Equipment: AKTA Explorer 100 preparative liquid chromatography system (GE Healthcare, i.e. the original Amershan Pharmacia Co.)

Chromatographic media: SP Sepharose 4 Fast Flow

Column Volume: 5.5 cm×20 cm

Buffer: 20 mM phosphate buffer pH 7.5, 10 mM DTT 20 mM phosphate buffer pH 7.5, 10 mM DTT, 2M NaCl Flow Rate: 25 mL/min Detector Wavelength: 280 nm Sample: the supernatant in 10 mM phosphate buffer pH7.5, 10 mM DTT, 300 mM NaCl in Example 2

Elution protocol: eluting undesired proteins with 400 mM NaCl, eluting the protein of interest with 500 mM NaCl, collecting 500 mM NaCl elutate, and finally getting about 1000 mL purified HPV16-L1 sample.

Purification of HPV16N30C-L1 by MC (Hydrophobic Interaction Chromatography)

Equipment: AKTA Explorer 100 preparative liquid chromatography system (GE Healthcare, i.e. the original Amershan Pharmacia Co.)

Chromatographic media: Butyl Sepharose 4 Fast Flow

Column Volume: 5.5 cm×20 cm

Buffer: 10 mM phosphate buffer pH 7.5, 10 mM DTT, 2M NaCl

Elution Buffer: 10 mM phosphate buffer pH 7.5, 10 mM DTT

Flow Rate: 20 mL/min

Detector Wavelength: 280 nm

Sample: the elutate from SP Sepharose 4 Fast Flow

Elution protocol: eluting undesired proteins with 1M NaCl, eluting the protein of interest with 800 mM NaCl and 500 mM NaCl.

Figure 2:
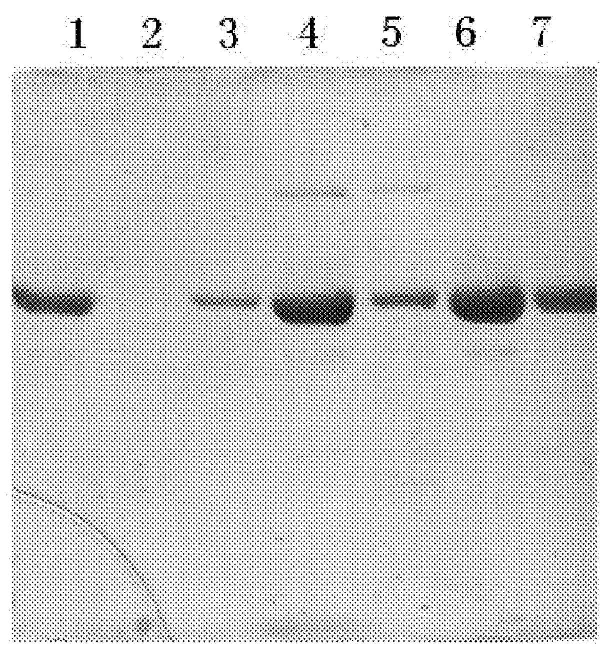

The elutate was collected when eluting with 800 mM and 500 mM NaCl. About 1300 ml purified HPV16N30C-L1 sample was obtained. 150 μL elutate collected when eluting with 800 mM/500 mM NaCl was added to 30 μL 6× loading buffer, and then the result solution was mixed thoroughly. After heating the solution in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 2. The concentration of the protein of interest was about 0.5 mg/ml, and the purity was greater than 98% according to SDS-PAGE.

EXAMPLE 4

Assembly of HPV16N30C-L1 VLPs

Equipment: Centrasette 5 Tangential Flow Filter (Pall Co.), retention MW 30 kDa.

Sample: 1500 mL HPV16N30C-L1 obtained in Example 3

Sample Concentration Sample was concentrated to 800 mL with the system tangential flow rate adjusted to 50 mL/min Sample Renaturation: Sample buffer was exchanged with 10 L renaturation buffer (50 mM PB pH 6.0, 2 mM $CaCl_2$, 2 mM $MgCl_2$, 0.5M NaCl, 0.003% Tween-80) thoroughly. When running the Tangential Flow Filter, the pressure was 0.5 psi and the tangential flow rate was 10 mL/min. When exchange was finished, the sample buffer was replaced with storage buffer (20 L PBS: 20 mM PB pH 6.5, 0.5M NaCl). The exchange volume was 20 L. The running pressure was 0.5 psi and the tangential flow rate was 25 mL/min. When the liquid exchange was finished, the sample was aseptically filtrated with a Pall filter (0.20 μm). The HPV16N30C-L1 VLPs were obtained.

EXAMPLE 5

Determination of the Morphology and Immunogenicity of HPV16N30C-L1 VLPs

Transmission Electron Microscopy (TEM) of HPV16N30C-L1 VLPs

Figure 3:
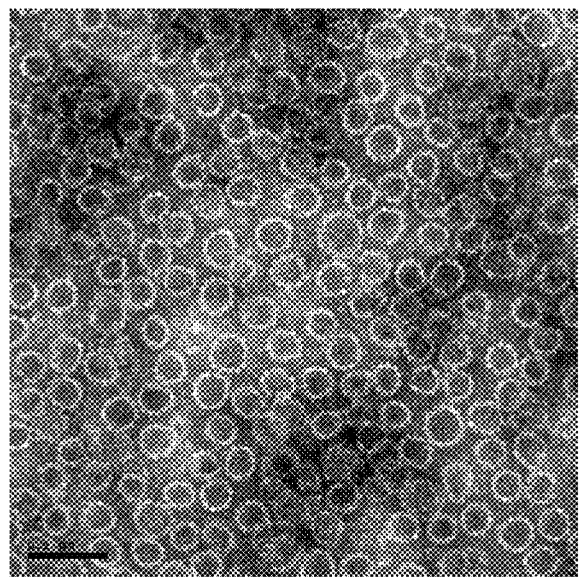
FIG. 3 shows the transmission electron microscopy (TEM) photograph of HPV16N30C-L1 VLPs obtained in Example 4, taken at 100,000× magnification, bar represents 0.1 μm. A great deal of VLPs in a radius of about 25 nm were observed in the visual field, wherein the particle size was consistant with the theoretic size and the particles were homogenous.

The equipment was a JEOL 100 kV Transmission Electron Microscope (100,000× magnification). HPV16N30C-L1 VLPs were negatively stained with 2% phosphotungstic acid at pH 7.0, and fixed on a copper grid. Results were shown in FIG. 3. It could be seen that the VLPs obtained in Example 4 had a radius of approximately 25 nm, and were homogenous and in a hollow form.

Dynamic Light-Scattering Measurement of HPV16N30C-L1 VLPs

Figure 4:
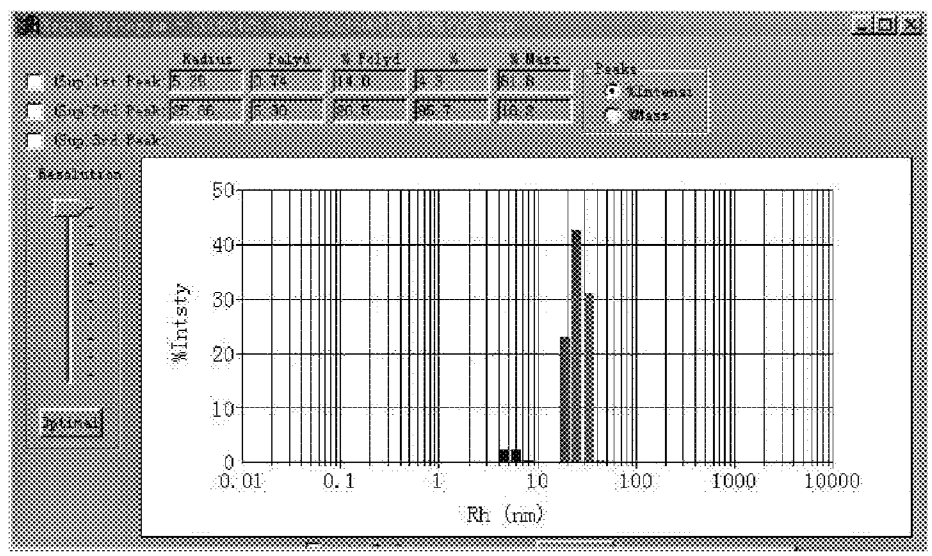
FIG. 4 shows Dynamic light-scattering measurement result of HPV16N30C-L1 VLPs obtained in Example 4. The result shows that HPV16N30C-L1 VLPs had a hydrodynamic radius of 25.86 nm and a particle reassembly rate of 95.7%.

DynaPro MS/X dynamic light-scattering instrument (including a temperature controller) (US Protein Solutions Co.) was used for light-scattering measurements. The regulation algorithm was used in the measurements. The sample was the one obtained in Example 4. The sample was passed through a 0.22 μm filter membrane prior to the measurement. Results were shown in FIG. 4. The result shows that HPV16N30C-L1 VLPs had a Hydrodynamic radius of 25.86 nm.

Establishment of Pseudovirion Neutralization Assay for HPV16

HPV can hardly be cultured in vitro, and the HPV host had a strong specificity. Thus, HPV can hardly be propagated in hosts other than human. That is, there was not an appropriate animal model for HPV. Therefore, in order to evaluate the immune productivity of HPV vaccine quickly, there was a need to establish a efficient model for in vitro neutralization assays.

In Vitro Infection Model of Pseudovirion: According to the characteristic that HPV VLP can package nucleic acids non-specifically, HPV pseudovirion was formed by expressing HPV L1 and L2 protein in cells, and by packaging viral DNA of episome or introducing reporter plasmids heterologously. Methods include expression systems based on recombinant viruses and cotransfection of multi-plasmids (see Yeager, M. D, Aste-Amezaga, M. et al (2000) Virology (278) 570-7).

The invention utilizes cotransfection of a multi-plasmid system. Some improvements were made as follows. An optimized calcium phosphate transfection method was established for the 293FT cell line, with a transfection efficiency of above 90%, which facilitate the production on a large scale. The resultant codon-optimized expression plasmid of HPV structural protein could express HPV L1 and L2 gene efficiently in mammalian cell lines, facilitating efficient assembly of pseudovirion.

Construction of HPV Pseudovirion:

P16L1h, p16L2h and pN31-EGFP (donated by Professor T. Schiller of NIH) contain genes for HPV16L1, HPV16L2, and GFP, respectively. These plasmids were purified using CsCl density gradient centrifugation as described in The Molecular Cloning Experiment Guide, (3rd edition). The purification procedure was as follows:

Plasmids were used to transform *E. coli* DH5α;

Single colonies were transferred into 500 mL LB culture medium and incubated in a shaking flask at 37° C. for 16 h;

Culture medium was centrifuged at 9,000 g for 5 min and the stains were collected;

The following substances were successively added to bacteria in each 1000 mL LB: 40 mL solution I (50 mM glucose, 25 mM Tris-Cl pH 8.0, 10 mM EDTA pH 8.0) and 2 ml 1 μg/μL RNase A), 40 mL solution II (0.2M NaOH, 1% SDS), and 48 mL solution III (60 mL 5M potassium acetate, 11.5 mL acetic acid, and 28.5 mL deionized water);

After placing on ice for 10 min, the mixture was centrifuged at 15,000 g for 20 min at 4° C.;

The supernatant was mixed with 0.6 volume of isopropyl alcohol, then was centrifuged again at 15,000 g for 30 min at 4° C.;

The supernatant was decanted into waste and the precipitation was washed with 70% ethanol;

The precipitation was dissolved in TE and the content of DNA was determined;

CsCl was dissolved in the solution of DNA (1 g DNA per 1.01 g CsCl), and then 100 μL 10 mg/mL EB solution was also dissolved in it;

The mixture was centrifuged using a Beckman NVT65 centrifuge at 62,000 rpm for 10 hr at 20° C.;

Closed circle DNA section was collected using an injector pinhead;

EB was extracted with equivalent volume of Isoamyl alcohol repeatedly for four times;

Three volumes of deionized water and eight volumes of dry ethanol were added to one volume of DNA solution, and then the mixture was centrifuged at 20000 g for 30 min at 4° C.;

The precipitation was collected and washed with 75% ethanol, and then dissolved in 1 mL TE;

The concentration of the DNA solution was determined, then the solution was stored in small packages at −20° C.

The purified p16L1h, p16L2h and pN31-EGFP co-transfected 293FT cells (Invitrogen) cultured on a 10 cm cell culture plate by calcium phosphate method. The calcium phosphate method was described as follows. 40 μg p16L1h, 40 μg p16L2h, and 40 μg pN31-EGFP were separately added to the mixture of 1 mL HEPES solution (125 μM HEPES/50 mL deionized water, at pH7.3 and 4° C.) and 1 mL 0.5M $CaCl_2$ solution. After mixing, 2 mL 2×HeBS solution (0.28M NaCl (16.36 g), 0.05M HEPES (11.9 g), 1.5 mM $Na_2HPO_4$ (0.213 g), dissolved in 1000 mL deionized water, at pH 6.96 and −70° C.) was added dropwise. After standing at room temperature for 1 min, the mixture was added to the 10 cm cell culture plate where the 293FT cells were cultured. The original culture medium was replaced with 10 ml complete medium (Invitrogen Co.) 6 hours later. 48 hours after transfection, the medium was decanted and the cells were washed twice with PBS. Then, the cells were collected and counted. Every $10^8$ cells were suspended in 1 mL cytolytic solution (0.25% Brij58, 9.5 mM $MgCl_2$). After lysing, cell lysate was centrifugated at 5,000 g for 10 min and the supernatant was collected. The Pseudovirion solution was obtained after adding 5M NaCl to the supernatant to a final concentration of 850 mM, then was stored in small packages at −20° C.

293FT cells (Invitrogen) were spread on a 96-well cell culture plate ($1.5\times10^4$ cells/well). Neutralization assay was performed five hours later. Serum samples were serially diluted with 10% DMEM half-by-half. 50 μL diluted samples were separately mixed with 50 μL Pseudovirion solutions diluted with 10% DMEM (moi=0.1). After incubating at 4° C. for 1 h, the mixture was added to the 96-well cell culture plate spread with 293FT cells. The mixture was then incubated for 72 h at 37° C. Neutralization titers of samples were estimated by observing fluorescence. Infection percentage of cells in each well was checked by flow cytometry (EPICS XL, American Beckman Coulter Co.). The exact titers of monoclonal antibodies or polyclonal antibodies were calculated. Infection percentage was the percentage of cells in the positive region minus the uninfected cells in the positive region.

Infection control percentage=(1−infection percentage of sample cell/infection percentage of negative cell)×100%

Neutralization titer was defined as the highest dilution multiple by which the infection control percentage was just above 50%. Monoclonal and polyclonal antibodies were considered as having neutralizing capacity if their infection control percentage was above 50% after 50 times dilutions.

Immune Protectivity of Animals Inoculated with HPV16 VLPs:

50% Effective Dose ($ED_{50}$) Assay in Mouse: HPV16N30C-L1 VLPs produced in Example 4 were adsorbed on aluminum hydroxide adjuvant, and then were diluted with vaccine diluents to four different concentrations at a ratio of 1:3 (i.e. 0.1 μg/mL, 0.033 μg/mL, 0.011 μg/mL and 0.004 μg/mL). In each experimental group, ten BALB/c mice were inoculated with 1 mL of the above vaccine by intraperitoneal injection. Serum was collected at the forth and fifth weeks after injection, and HPV neutralizing antibodies were evaluated by the EIA and pseudovirion neutralization assays. After the last serum collection, the mice were sacrificed. The control group includes ten BALB/c mice.

Cutoff value for EIA was average negative value plus 0.16 (if average negative value was below 0.05, 0.05 was used in the calculation). Before inoculation, all BALB/c mice show negative in the HPV neutralizing antibody assays, results were shown in Table 1.

TABLE 1

$ED_{50}$ result of HPV16N30C-L1 VLPs in BALB/c Mice by EIA Assay

| | | 4 weeks | | 5 weeks | |
|---|---|---|---|---|---|
| Concentration μg/mL | Number of mouse | Positive number | Positive rate (%) | Positive number | Positive rate (%) |
| 0.100 | 10 | 10 | 100.00 | 10 | 100.00 |
| 0.033 | 10 | 10 | 100.00 | 10 | 100.00 |
| 0.011 | 10 | 6 | 66.67 | 6 | 66.67 |
| 0.004 | 10 | 2 | 14.29 | 2 | 14.29 |

ED50 was calculated according to the Reed-Muench method. After inoculation, blood was collected for detecting $ED_{50}$ at the forth and fifth week. HPV16N30C-L1 VLPs had a $ED_{50}$ of 0.019 μg at the forth week and 0.011 μg at the fifth week. Therefore, immunization in these dosages could induce high levels of neutralizing antibodies. The efficacy of these dosages was far less than that of 0.1 μg.

Results in the pseudovirion neutralization assay could only be accepted when more than 20% of the cells in the negative control group and none of the cells in the positive control group fluoresce. It was considered as a positive result when less than 50% of the cells in the negative control group fluoresce. Results were shown in Table 2.

TABLE 2

$ED_{50}$ result of HPV16N30C-L1 VLPs in BALB/c Mice in Pseudovirion Neutralization Assay

| | | 4 weeks | | 5 weeks | |
|---|---|---|---|---|---|
| Concentration μg/mL | number of mice | Positive number | Positive rate (%) | Positive number | Positive rate (%) |
| 0.100 | 10 | 10 | 100 | 10 | 100 |
| 0.033 | 10 | 10 | 100 | 9 | 92 |
| 0.011 | 10 | 1 | 10 | 3 | 27 |
| 0.004 | 10 | 0 | 0 | 0 | 0 |

ED50 was calculated according to the Reed-Muench method. After inoculation, blood was collected for detecting $ED_{50}$ at the forth and fifth week. HPV16N30C-L1 VLPs had a $ED_{50}$ of 0.019 μg at the forth week and 0.011 μg at the fifth week. Therefore, immunization in these dosages could induce high levels of neutralizing antibodies. The efficacy of these dosages was far less than that of 0.1 μg.

Female rabbits (general level), 6-8 weeks old, were purchased from the Disease Prevention and Control Center of Guangxi province, where they were raised. HPV16N30C-L1 VLPs prepared in Example 4, were mixed with equal amount of complete Freund's Adjuvant for the first immunization. For the booster, HPV16N30C-L1 VLPs were mixed with incomplete Freund's Adjuvant. Rabbits were immunized via muscle injection, with 100 μg per rabbit for the first immunization, and separately with 50 μg per rabbit for the booster at week 4, 10. After immunization, external vein blood was collected every week, and serum was separated and stored for detection.

Female goats (general level), 6-8 weeks old, were purchased from the Disease Prevention and Control Center of Guangxi province, where they were raised. HPV16N30C-L1 VLPs prepared in Example 4, were mixed with equal amount of complete Freund's adjuvant for the first immunization. For the booster, HPV16N30C-L1 VLPs were mixed with incomplete Freund's adjuvant. Goats were immunized via muscle injection, with 1 mg per goat for the first immunization, and with 0.5 mg per goat for the booster separately at weeks 4, 10 and 18. After immunization, external vein blood was collected, and serum was separated and stored for detection.

Neutralization titers of the anti-serums were evaluated using a pseudovirion-based neutralization cell model assay. As shown in FIGS. 5 and 6, the vaccine produced from HPV16N30C-L1 VLPs prepared in Example 4 had good immunogenicity, could induce neutralizing antibodies with a high titer in animals, and could be used as an effective vaccine for the prevention of HPV infection.

Immune Response of Rhesus Monkeys Inoculated With HPV16/18 Bivalent Vaccine

Female rhesus monkeys (General level), 2 years old, were purchased from the Disease Prevention and Control Center of Guangxi Province, where they were raised. HPV16N30C-L1 prepared in Example 4 were adsorbed on aluminum hydroxide adjuvants, and HPV18N65C-L1 VLPs prepared according to the method similar to that of Example 4 were also adsorbed on aluminum hydroxide adjuvants. Then, the two were mixed at a ratio of 2:1 by weight to produce a bivalent HPV16/18 vaccine. Each dose (0.5 ml) contained 40 μg HPV16N30C-L1 VLPs, 20 μg HPV18N65C-L1 VLPs and 0.6 mg aluminum hydroxide. The Rhesus monkeys were separately administrated with 5 μg, 10 μg and 20 μg HPV 16 by injection in deltoid of the upper-limb (on triplicate). All the candidate animals show the total IgG antibodies and neutralizing antibodies against HPV 16 were negative before immunization. Vaccine was administered at 0 and 4 weeks. The animals were raised for 9 weeks, and blood was collected every week. Blood samples were stored at 37° C. for 1.5 h, and then centrifuged at 10,000 rpm for 5 min. Serum was collected to assay titers of total IgG and neutralizing antibodies against HPV16 and HPV18. Similar assay methods were used for the two types of antibodies.

As shown in FIG. 7 and FIG. 8, HPV16N30C-L1 VLPs according to the invention could induce high titers of total IgG and neutralizing antibodies, exceeding 20,000 at week 9 after the first immunization. HPV16N30C-L1 VLPs had good immunogenicity and could be used as an effective vaccine for the prevention of HPV16 infection. Also, HPV18N65C-L1 VLPs of the Bivalent Vaccine could induce high titers of total IgG and neutralizing antibodies against HPV18, exceeding 20,000 at week 9 after the first immunization, as shown in FIG. 9 and FIG. 10. It was shown that HPV18N65C-L1 VLPs had good immunogenicity and could also be used as an effective vaccine for the prevention of HPV18 infection.

The amino acid sequence of HPV18N65C-L1 is shown in SEQ ID NO. 9 as follows.

```
Met Arg Pro Ser Asp Asn Thr Val Tyr Leu Pro Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Pro Ala Gly Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
```

-continued

```
        260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
        355                 360                 365

Asp Leu Gln Phe Ile Phe Gln Leu Cys Thr Ile Thr Leu Thr Ala Asp
    370                 375                 380

Val Met Ser Tyr Ile His Ser Met Asn Ser Ser Ile Leu Glu Asp Trp
385                 390                 395                 400

Asn Phe Gly Val Pro Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
        435                 440                 445

Leu Lys Glu Lys Phe Ser Leu Asp Leu Asp Gln Tyr Pro Leu Gly Arg
    450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500
```

Immune Protectivity of Mice Inoculated with HPV6/11/16/18 Quadrivalent Vaccine

Four SPF BALB/c mice, 4-5 weeks old, were used. HPV6N5C-L1, HPV11N4C-L1 and HPV18N65C-L1 VLPs, prepared according to the method similar to that of Example 4, were mixed at a ratio of 1:2:2:1 (by weight), wherein the final concentrations of them were 40 μg/mL, 80 μg/mL, 80 μg/mL and 40 μg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 μg HPV6N5C-L1, 10 μg HPV18N65C-L1, 20 μg HPV11N4C-L1, and 20 μg HPV16N30C-L1 per mouse. The booster was administered every two weeks. The amount for the booster was 20 μg HPV6N5C-L1, 20 μg HPV18N65C-L1, 40 μg HPV11N4C-L1, and 40 μg HPV16N30C-L1 per mouse.

After immunization, external vein blood was collected every week and serum was separated. The titers of neutralizing antibodies against HPV6, HPV11, HPV16 and HPV18 in immunized mice were separately determined according to the method of Example 5.

Results were shown in FIG. 11, indicating that HPV6/11/16/18 quadrivalent vaccine, prepared by blending HPV6N5C-L1, HPV11N4C-L1, HPV16N30C-L1 and HPV18N65C-L1 VLPs prepared in Examples 1-4, had good immunogenicity, could induce neutralizing antibodies with a high titer against HPV 6, HPV 11, HPV 16, and HPV 18 in animals, and could be used as an effective vaccine for the prevention of HPV6/HPV11/HPV16/HPV18 infection (in addition to the Freund's adjuvants used in the experiments, the vaccine could be prepared by blending the four HPV6N5C-L1, HPV11N4C-L1, HPV16N30C-L1 and HPV18N65C-L1 VLPs with aluminum hydroxide or aluminum phosphate adjuvants available commercially or self-prepared).

The Amino Acid Sequence of HPV6N5C-L1 is showed in SEQ ID NO 10.

```
Met Asp Ser Thr Val Tyr Val Pro Pro Pro Asn Pro Val Ser Lys Val
1               5                   10                  15

Val Ala Thr Asp Ala Tyr Val Thr Arg Thr Asn Ile Phe Tyr His Ala
            20                  25                  30
```

-continued

```
Ser Ser Ser Arg Leu Leu Ala Val Gly His Pro Tyr Phe Ser Ile Lys
        35                  40                  45

Arg Ala Asn Lys Thr Val Val Pro Lys Val Ser Gly Tyr Gln Tyr Arg
    50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
            100                 105                 110

His Pro Phe Leu Asn Lys Tyr Asp Asp Val Glu Asn Ser Gly Ser Gly
        115                 120                 125

Gly Asn Pro Gly Gln Asp Asn Arg Val Asn Val Gly Met Asp Tyr Lys
    130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
        195                 200                 205

Lys Ser Asp Val Pro Ile Asp Ile Cys Gly Thr Thr Cys Lys Tyr Pro
    210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
        275                 280                 285

Gly Ser Leu Val Ser Ser Glu Ala Gln Leu Phe Asn Lys Pro Tyr Trp
    290                 295                 300

Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
            340                 345                 350

Glu Tyr Met Arg His Val Glu Glu Tyr Asp Leu Gln Phe Ile Phe Gln
        355                 360                 365

Leu Cys Ser Ile Thr Leu Ser Ala Glu Val Val Ala Tyr Ile His Thr
    370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
        435                 440                 445

Glu Leu Asp Gln Tyr Pro Leu Gly Arg Lys Phe Leu Leu Gln Ser Gly
    450                 455                 460
```

-continued

```
Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495
```

The Amino Acid Sequence of HPV11N4C-L1 is shown in SEQ ID NO: 11:

```
Met Ser Asp Ser Thr Val Tyr Val Pro Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365
```

-continued

```
Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys
```

The Amino Acid Sequence of HPV18N65C-L1 is shown in SEQ ID NO. 9.

The experimental results show that the vaccine that was formed by HPV16N30C-L1 VLPs prepared in Example 4 (in addition to the Freund's adjuvants used in the experiments, aluminum hydroxide or aluminum phosphate adjuvants available commercially or self-prepared could also be used) had good immunogenicity could induce neutralizing antibodies with a high titer in animals, and could be an effective vaccine useful for the prevention of HPV infection.

EXAMPLE 6

The truncated HPV16L1 proteins set forth in SEQ ID NOs: 1, 2, 3, 4, 5, and 7 were prepared according to the techniques used in examples 1-5. All these truncated proteins could be assembled into VLPs.

The invention claimed is:

1. A truncated recombinant human papilloma virus type 16 (HPV 16) L1 protein that is truncated at its N-terminus, wherein the protein consists of the amino acid sequence of SEQ ID NO:6 or 7.

2. A recombinant polynucleotide encoding a HPV16 L1 protein that is truncated at its N-terminus, wherein the protein consists of the amino acid sequence of SEQ ID NO:6 or 7.

3. A recombinant vector comprising the polynucleotide of claim 2.

4. An isolated cell comprising the vector of claim 3.

5. A composition comprising the protein of claim 1.

6. A HPV16 virus-like particle (VLP) comprising the protein of claim 1.

7. A method for producing a HPV16 L1 protein, the method comprising:

a) expressing a HPV16 L1 gene encoding the HPV16 L1 protein of claim 1 in an *E. coli* expression system;

b) disrupting the *E. coli*, which has expressed the HPV16 L1 protein, in a solution with a salt concentration of 100 mM to 600 mM, and isolating a supernatant;

c) decreasing the salt concentration of the supernatant to 0 mM to 100 mM using water or a low salt solution to produce a precipitate;

d) collecting the precipitate; and e) redissolving the precipitate in a solution with a salt concentration of 150 mM to 2500 mM, adding a reductant to it, and then isolating the resultant solution, wherein the resultant solution contains the HPV16 L1 protein with a purity of at least 50%.

8. A vaccine for the prevention of cervical cancer, comprising:

the HPV16 VLP of claim 6 and a carrier or excipient.

9. A method for preventing cervical cancer, comprising administering a vaccine comprising a preventively effective amount of the HPV16 L1 protein of claim 1, a VLP comprising the protein of claim 2, or a vaccine comprising a HPV16 VLP comprising the protein of claim 2 to an individual in need of it.

10. A method for providing a VLP of HPV 16 L1 protein, comprising:

a) expressing the polynucleotide of claim 2 in an *E. coli* expression system;

b) disrupting the *E. coli*, which has expressed the HPV 16 L1 protein, in a solution with a salt concentration of 100 mM to 600 mM, and isolating a supernatant;

c) decreasing the salt concentration of the supernatant to 0 mM to 100 mM using water or a low salt solution to produce a precipitate;

d) collecting the precipitate;

e) redissolving the precipitate in a solution at a salt concentration of 150 mM to 2500 mM, adding a reductant to it, and then isolating the resultant solution, wherein the resultant solution contains the HPV 16 L1 protein with a purity of at least 50%;

f) further purifying the HPV 16 L1 protein by chromatography; and g) removing the reductant from the HPV 16 L1 protein.

11. A method for producing a vaccine for prevention of cervical cancer, comprising mixing the VLP of claim 6, and optionally with one or more VLPs selected from the group consisting of VLPs of HPV types 6, 11, 18, 31, 33, 45, 52, and 58, with carriers or excipients for vaccines.

12. The vaccine of claim 8, wherein the HPV16 VLP comprises a protein comprising the amino acid sequence of SEQ ID NO:6.

13. The vaccine of claim 8, further comprising at least one HPV VLP selected from the group consisting of VLPs of HPV types 6, 11, 18, 31, 33, 45, 52, and 58.

14. The vaccine of claim 13, wherein the HPV18 VLP comprises a protein comprising the amino acid sequence of SEQ ID NO:9.

15. The vaccine of claim 13, wherein the HPV6 VLP comprises a protein comprising the amino acid sequence of SEQ ID NO:10.

16. The vaccine of claim 13, wherein the HPV11 VLP comprises a protein comprising the amino acid sequence of SEQ ID NO:11.

17. The vaccine of claim 8, wherein the HPV16 VLP comprises a protein comprising the amino acid sequence of SEQ ID NO:7.

* * * * *